United States Patent
Arabian et al.

(10) Patent No.: US 11,285,025 B2
(45) Date of Patent: *Mar. 29, 2022

(54) PROSTHETIC HYDRAULIC JOINT WITH ACCUMULATOR AND METHODS FOR CONTROLLING JOINT

(71) Applicant: OTTOBOCK SE & CO. KGAA, Duderstadt (DE)

(72) Inventors: Adam Arabian, Silverdale, WA (US); David Alan Boone, Seattle, WA (US); Ben Gilbert Macomber, Shoreline, WA (US); Tyler Butel, Edmond, OK (US); Robert Dustin Lane, Seattle, WA (US)

(73) Assignee: OTTOBOCK SE & CO. KGAA

( * ) Notice: Subject to any disclaimer, the term of this patent is extended or adjusted under 35 U.S.C. 154(b) by 216 days.

This patent is subject to a terminal disclaimer.

(21) Appl. No.: 16/419,614

(22) Filed: May 22, 2019

(65) Prior Publication Data

US 2019/0269529 A1 Sep. 5, 2019

Related U.S. Application Data

(60) Continuation of application No. 15/809,787, filed on Nov. 10, 2017, now Pat. No. 10,314,724, which is a
(Continued)

(51) Int. Cl.
*A61F 2/66* (2006.01)
*A61F 2/74* (2006.01)
(Continued)

(52) U.S. Cl.
CPC .............. *A61F 2/6607* (2013.01); *A61F 2/70* (2013.01); *A61F 2/741* (2021.08); *A61F 2/74* (2021.08);
(Continued)

(58) Field of Classification Search
CPC .................................................... A61F 2/6607
(Continued)

(56) References Cited

U.S. PATENT DOCUMENTS

| | | | |
|---|---|---|---|
| 6,443,993 B1 | 9/2002 | Koniuk | |
| 7,029,500 B2 | 4/2006 | Martin | |

(Continued)

FOREIGN PATENT DOCUMENTS

SE 94003803 A 8/1995

OTHER PUBLICATIONS

International Search Report and Written Opinion dated Jan. 3, 2013, issued in corresponding International Application No. PCT/US2012/045318, filed Jul. 2, 2012, 8 pages.

*Primary Examiner* — David H Willse
(74) *Attorney, Agent, or Firm* — Holland & Hart LLP

(57) ABSTRACT

A prosthetic foot assembly is disclosed. The assembly includes a pivoting ankle joint with a hydraulic system, a prosthetic foot connected to the distal side of the ankle joint, and, at the proximal side, the ankle joint includes a transducer with pyramid adaptor for attaching to a pylon. The ankle joint sensor provides data collection during the stance and optionally, the swing, phases of walking using, for example, strain gages and accelerometers. Also disclosed are methods for real-time feature extraction. Key parameters are captured to which are applied linear, fuzzy logic, neural net, or generic algorithms to determine current state (walking flat, uphill, downhill etc.) in real time and execute changes to the angle between the ankle and foot almost instantaneously based on those parameters.

20 Claims, 16 Drawing Sheets

Related U.S. Application Data division of application No. 13/540,388, filed on Jul. 2, 2012, now Pat. No. 9,820,871.

(60) Provisional application No. 61/504,095, filed on Jul. 1, 2011.

(51) Int. Cl.
*A61F 2/70* (2006.01)
*A61F 2/68* (2006.01)
*A61F 2/50* (2006.01)
*A61F 2/76* (2006.01)

(52) U.S. Cl.
CPC ....... *A61F 2/748* (2021.08); *A61F 2002/5003* (2013.01); *A61F 2002/5006* (2013.01); *A61F 2002/5018* (2013.01); *A61F 2002/5033* (2013.01); *A61F 2002/6854* (2013.01); *A61F 2002/701* (2013.01); *A61F 2002/704* (2013.01); *A61F 2002/764* (2013.01); *A61F 2002/765* (2013.01); *A61F 2002/7625* (2013.01); *A61F 2002/7635* (2013.01); *A61F 2002/7645* (2013.01); *A61F 2002/7665* (2013.01)

(58) Field of Classification Search
USPC .................................................... 623/47–52
See application file for complete search history.

(56) References Cited

U.S. PATENT DOCUMENTS

| | | | |
|---|---|---|---|
| 7,637,959 | B2 | 12/2009 | Clausen et al. |
| 7,886,618 | B2 | 2/2011 | Macomber et al. |
| 7,922,774 | B2 | 4/2011 | Macomber et al. |
| 7,985,265 | B2 | 7/2011 | Moser et al. |
| 8,111,165 | B2 | 2/2012 | Ortega et al. |
| 8,215,186 | B2 | 7/2012 | Macomber et al. |
| 9,820,871 | B2* | 11/2017 | Arabian .............. A61F 2/70 |
| 10,314,724 | B2* | 6/2019 | Arabian ............ A61F 2/6607 |
| 2002/0045946 | A1 | 4/2002 | Habecker |
| 2002/0138153 | A1 | 9/2002 | Koniuk |
| 2006/0155385 | A1 | 7/2006 | Martin |
| 2006/0224246 | A1 | 10/2006 | Clausen et al. |
| 2006/0224247 | A1 | 10/2006 | Clausen et al. |
| 2008/0058959 | A1 | 3/2008 | Bedard et al. |
| 2008/0262635 | A1 | 10/2008 | Moser et al. |
| 2009/0030530 | A1 | 1/2009 | Martin |
| 2009/0222105 | A1 | 9/2009 | Clausen |
| 2010/0161077 | A1 | 6/2010 | Boone |
| 2011/0160871 | A1 | 6/2011 | Boone |
| 2011/0196509 | A1* | 8/2011 | Jansen ............ B25J 17/0241 623/26 |
| 2012/0119912 | A1 | 5/2012 | Ortega et al. |

* cited by examiner

PROSTHETIC HYDRAULIC JOINT WITH ACCUMULATOR AND METHODS FOR CONTROLLING JOINT

CROSS-REFERENCE TO RELATED APPLICATIONS

This application is a continuation of U.S. patent application Ser. No. 15/809,787, filed Nov. 10, 2017, now U.S. Pat. No. 10,314,724, issued Jun. 11, 2019, which is a divisional of U.S. patent application Ser. No. 13/540,388, filed Jul. 2, 2012, now U.S. Pat. No. 9,820,871, issued Nov. 21, 2017, which claims the benefit of U.S. Provisional Application No. 61/504,095, filed Jul. 1, 2011, the disclosures of which are fully incorporated herein expressly by reference.

BACKGROUND

The field of prosthetics has seen many advances made to enhance the quality of life by improving mobility and returning functionality to persons that have suffered the loss of a lower limb. A prosthesis that replaces a lower limb, including the ankle joint and foot, can be tuned or aligned for a certain type of ambulation, say, walking on an even surface. While a lower limb amputee may engage in walking on even surfaces a great majority of the time, there will inevitably be occasions where the surface is not even, and the prosthesis performs poorly. While a person having both of his/her legs may unconsciously accommodate the change in terrain quickly and easily, a person using a prosthesis can not readily make such adjustment. A person wearing a prosthesis that is rigidly fixed in one position must learn to cope, by perhaps, adopting unnatural walking stances, or shifting weight in a particular way to increase balance or avoid injury. It is difficult to build a prosthesis that is as adaptable to different conditions as a human foot. However, some have sought to address the problem by building prosthetic ankle joints that pivot, and/or including a dampening motion during walking. More functionality of prosthetic ankle joints is needed to increase the ability to cope with different situations.

SUMMARY

A prosthetic foot assembly is disclosed. The assembly includes a pivoting ankle joint with a hydraulic system, a prosthetic foot connected to the distal side of the ankle joint, and at the proximal side, the ankle joint includes a transducer with an adaptor for attaching to a pylon. The pylon is connected to a socket that receives an amputated limb. The foot assembly includes a universal distal attachment allowing accommodation of various prosthetic feet.

The hydraulic system of the ankle joint includes a dual piston assembly with respective antagonistic cams, which remain in constant contact with pistons. The system includes a posterior piston and an anterior piston, respectively placed in front of and behind a pivoting connection. The pistons each include an integral accumulator with restrictors and check valves. An accumulator receives and releases hydraulic fluid gradually. For example, when hydraulic fluid enters a cylinder, the accumulator receives some hydraulic fluid, depending on the pressure, and if the pressure overcomes the force of a spring restricting the entrance to the accumulator. In this case, the accumulator is a cylinder/subpiston within the main piston. Each piston has a sub-piston inside which provides temperature compensation by restricting flow to slow the flow rate rather than allowing angular movement to be "free" upon loading. This can be performed by: a) a small restrictor orifice or b) shear thickening fluid. Flow from the piston can be relieved through a one-way check valve to keep the pistons in constant contact with cams.

The heel (posterior) accumulator and toe (anterior) accumulator are restricted at different rates to accommodate differences in gait pattern (e.g., heel moment being significantly less than toe). Flow can be controlled through the use of a digital state valve with dual paths between the dual pistons/accumulators.

In one embodiment, the ankle joint can provide dorsiflexion bias for toe clearance. The compliance built in by compression of the accumulators allows the posterior piston to push up, and the anterior piston recedes to bring the toe up a small amount at swing phase. The spring force of the posterior accumulator can be greater than the spring force of the anterior accumulator.

Also disclosed are methods for controlling the ankle joint. The ankle joint/transducer provides data collection during the stance and swing phases of walking using, for example, strain gages and accelerometers.

The methods provide for real-time feature extraction. Key parameters are captured to which are applied linear, fuzzy logic, neural net, or generic algorithms to determine current state (walking flat, uphill, downhill etc.) in real time and execute changes to a plantarflexion angle between ankle and foot almost instantaneously (within first step, for example) based on those parameters. In some cases, a determination can be made prior to a complete step being recorded—certain conditions require or are highly dependant on only a single factor that is easily extracted sufficiently early in stance phase as to allow for initiation of accommodation while still in that stance phase.

Alternatively, parameters captured in the swing phase may provide sufficient indication as to allow preparatory valve positioning (opening) subject to confirmation of the stance phase data. In some methods, it is preferable that no decisions be made solely on swing phase accelerometry, but, in other embodiments, some changes may be "prepared" based on the swing phase and small changes executed with the possibility of correction if the swing phase data analysis was erroneous.

The methods may use natural moments induced in walking to affect microprocessor controlled changes. The methods use impedance control of joint position—instead of "forcing" the ankle to a given position, it is "allowed" to go to a given position under the natural moments induced by the patient. A patient is anyone that wears the ankle joint. User is synonymous with patient.

The methods may use concurrent voting and confirmation using two or more algorithms.

In some embodiments, methods may use parameters only from the stance phase, in other embodiments, methods may use parameters only from the swing phase. In some embodiments, methods may use parameters from the stance phase and the swing phase.

In some embodiments, the prosthesis assembly may further include a passive knee joint with control of the passive knee based on the active ankle behavior. A fully passive or passive stance phase knee can be modified and may be controlled based on variations of ankle angle. This would be either standalone or bi-directional feedback to a controlled knee The ankle joint may include a digital bus connection to sensor system.

In some embodiments, the ankle joint can be constructed with multi-axial movement in the anterior/posterior plane and the right/left plane.

In some embodiments, the ankle joint may have the ability to document various key parameters that may be used to assess functionality levels or to meet compliance with certain health organization's requirements. For example, the ankle joint may be configured to communicate with Internet-based products by recording data either through in-clinic testing or in-field recording of events and produce a report for the prosthetist for documentation of need—the ankle joint reduces moments at the socket by "X" percent when going up "Y" percent grade, which correlates to "Z" effect on their long term health, where X, Y, and Z, are parameters determined by the specific organization or agency. Documentation could be a discrete in-office test of one slope, stairs, etc. or could be a field recording over the span of a month to indicate the effect the ankle joint has in a patient's normal life. "Patient" is used herein to mean any person wearing the ankle joint system.

In some embodiments, the ankle joint is in communication with a mobile phone or mobile device that the patient carries. A mobile phone or mobile device based application can be used to view the current state, set preferred states (such as dependent on various shoes), override system logic, shutdown, and communicate with prosthetist via email or application.

In some embodiments, a method for controlling a prosthetic ankle joint employing a processor and a sensor, is disclosed. The method may include determining if a prosthetic ankle joint is weight bearing, if the prosthetic ankle joint is weight bearing, determining if a stance phase is qualified to be a true stance phase and of a patient ambulating, if the stance phase is qualified to be a true stance phase, determining a ground slope or a speed of the patient, and controlling the angular alignment of the prosthetic ankle joint based on the ground slope or speed, and if the prosthetic ankle joint is not weight bearing, locking or relaxing the ankle joint.

In some embodiments, the method may further include collecting training gait data from the patient with a normal gait, and comparing the training gait data to data that is collected when the ankle joint is weight bearing, and based on the comparison qualifying the stance phase.

In some embodiments, the method may further include collecting training gait data from the patient walking on a level ground and at a normal speed, and determining a home position for the ankle joint based on the level ground and normal speed.

In some embodiments, the method may further include controlling the ankle joint at the home position when a level ground slope is detected.

In some embodiments, the method may further include controlling the ankle joint at the home position when a normal speed is detected.

In some embodiments, the method may further include collecting training gait data from a patient with a normal gait, comparing the training gait data to data that is collected from the qualified stance phase, and, based on the comparison, detecting the ground slope or speed.

In some embodiments, the method may further include dorsiflexing the prosthetic ankle joint when the ground slope is detected to be uphill.

In some embodiments, the method may further include plantarflexing the prosthetic ankle joint when the ground slope is detected to be downhill.

In some embodiments, the method may further include dorsiflexing the prosthetic ankle joint when the patient is detected to be walking slowly.

In some embodiments, the method may further include plantarflexing the prosthetic ankle joint when the patient is detected to be walking fast.

In some embodiments, the method may further include determining if the patient is ascending stairs or descending stairs if the stance phase is qualified to be a true stance phase.

In some embodiments, the method may further include determining anterior moment and posterior moment during a stance phase and comparing the anterior moment and posterior moment to training data.

In some embodiments, the method may further include detecting downhill when a maximum anterior moment is less than a maximum anterior moment of the training data and a maximum posterior moment is greater than a maximum posterior moment of the training data.

In some embodiments, the method may further include detecting uphill when a maximum anterior moment is greater than a maximum anterior moment of the training data and a maximum posterior moment is less than a maximum posterior moment of the training data.

In some embodiments, the method may further include detecting ascending stairs when an axial force is greater than an axial force of the training data and a posterior or anterior moment is greater than a posterior or anterior moment of the training data.

In some embodiments, the method may further include detecting descending stairs when an axial force is greater than an axial force of the training data and a posterior or anterior moment is greater than a posterior or anterior moment of the training data.

In some embodiments, the method may further include detecting if a keel angle is greater than a predetermined value and an anterior moment is greater than a predetermined value, for a specified time period, when the ankle joint is not weight bearing.

In some embodiments, the method may further include locking the ankle joint in response to detecting a keel angle is greater than a predetermined value and an anterior moment is greater than a predetermined value for a specified time period.

In some embodiments, the method may further include relaxing the ankle joint in response to not detecting a keel angle is greater than a predetermined value and an anterior moment is greater than a predetermined value for a specified time period.

In some embodiments, when the ankle joint is relaxed, the method may further include detecting at least one condition such as, the ankle joint is weight bearing, the ankle joint rate of motion exceeds a predetermined value, or the axial force rate of change exceeds a predetermined value, and, in response to detecting the one condition, moving the ankle to a home position determined from training gait data.

In some embodiments, the method may further include plantarflexing the ankle joint when a posterior moment is sensed during a stance phase.

In some embodiments, the method may further include dorsiflexing the ankle joint when an anterior moment is sensed during a stance phase.

In some embodiments, the method may further include determining if a swing phase is qualified to be a true swing phase of a patient ambulating, and if the stance phase and swing phase are qualified to be a true stance phase and swing phase of a person ambulating, determining a ground slope or a speed of the patient.

In some embodiments, the method may further include collecting training gait data from the patient with a normal gait, and comparing the training gait data to data that is collected when the ankle joint is weight bearing, and based on the comparison qualifying the stance and swing phase.

In some embodiments, the method may further include collecting training gait data from a patient with a normal gait, comparing the training gait data to data that is collected from the qualified stance and swing phase, and based on the comparison detecting the ground slope or speed.

In the embodiments of the method described, the various embodiments may include one, more than one, or all of the features of the other embodiments.

In some embodiments, a prosthetic ankle joint is disclosed. The ankle joint may include a base having a pivot secured to a body, a first and second piston in contact with the base, the body having a first and second cylinder within which the first and second pistons are placed, wherein the first cylinder and piston are placed anteriorly to the pivot, and the second cylinder and piston are placed posteriorly to the pivot, a hydraulic system connecting the first and second cylinders, wherein the system comprises one or more values to control transfer of fluid between the first and second cylinders, and a processor programmed with instructions to control the one or more valves.

In some embodiments, the prosthetic ankle joint may further include a first and second cam on the base, wherein the first cam supports the first piston, and the second cam supports the second piston, and the cams have a parabolic upper surface.

In some embodiments, the prosthetic ankle joint may further include in the first and second piston, a hydraulic fluid accumulator comprising a subpiston, and a spring biasing the subpiston within a chamber, wherein the chamber is allowed to receive and expel hydraulic fluid to and from the cylinder corresponding with the accumulator.

In some embodiments, the prosthetic ankle joint may further include a transducer connected to the upper side of the ankle joint, and a foot connected to the lower side of the base.

In the embodiments of the prosthetic ankle joint described, the various embodiments may include one, more than one, or all of the features of the other embodiments.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

A transducer can be used to measure the forces and moments acting on the prosthesis socket. When a transducer is attached to the exterior lower end of the prosthesis socket, the transducer is able to sense the forces and moments at the interface of the lower end of the prosthesis socket. Furthermore, because the attachment and adjustment point of the prosthesis socket to the pylon is at the bottom of the socket, a transducer being placed at this position, which corresponds to the position where the socket can be adjusted spatially, allows the transducer to be able to record moments that are experienced by the socket at the adjustable interface. The transducer may include a pyramid adaptor that is used for coupling a prosthesis socket to a pylon. The pyramid adaptor allows the prosthesis and pylon to be aligned along an anterior/posterior plane and in a right/left plane. As the prosthesis wearer walks using the prosthesis with transducer, the moments experienced at the interface of the lower end of the prosthesis socket along the anterior/posterior plane and the right/left plane can be measured and recorded.

Transducers, such as the one described, can be used for other purposes besides measuring moments at the interface of the socket and pylon. Disclosed herein is a prosthetic ankle joint with hydraulic actuators, and a transducer. Also disclosed are methods to configure the ankle joint from information gathered from the transducer. The ankle joint can pivot so as to plantarflex and dorsiflex the foot. The ankle joint can determine various weight and non-weight bearing activities. The ankle joint can dynamically adjust to provide an optimum plantarflexion angle when attached to a prosthetic foot depending on the activity the patient is presently engaged in.

A suitable transducer is provided in U.S. Pat. No. 7,886,618, incorporated herein expressly by reference. However, other transducers that are capable of measuring moments, axial forces, such as via the use of strain gauges may also be suitable.

Figure 1:
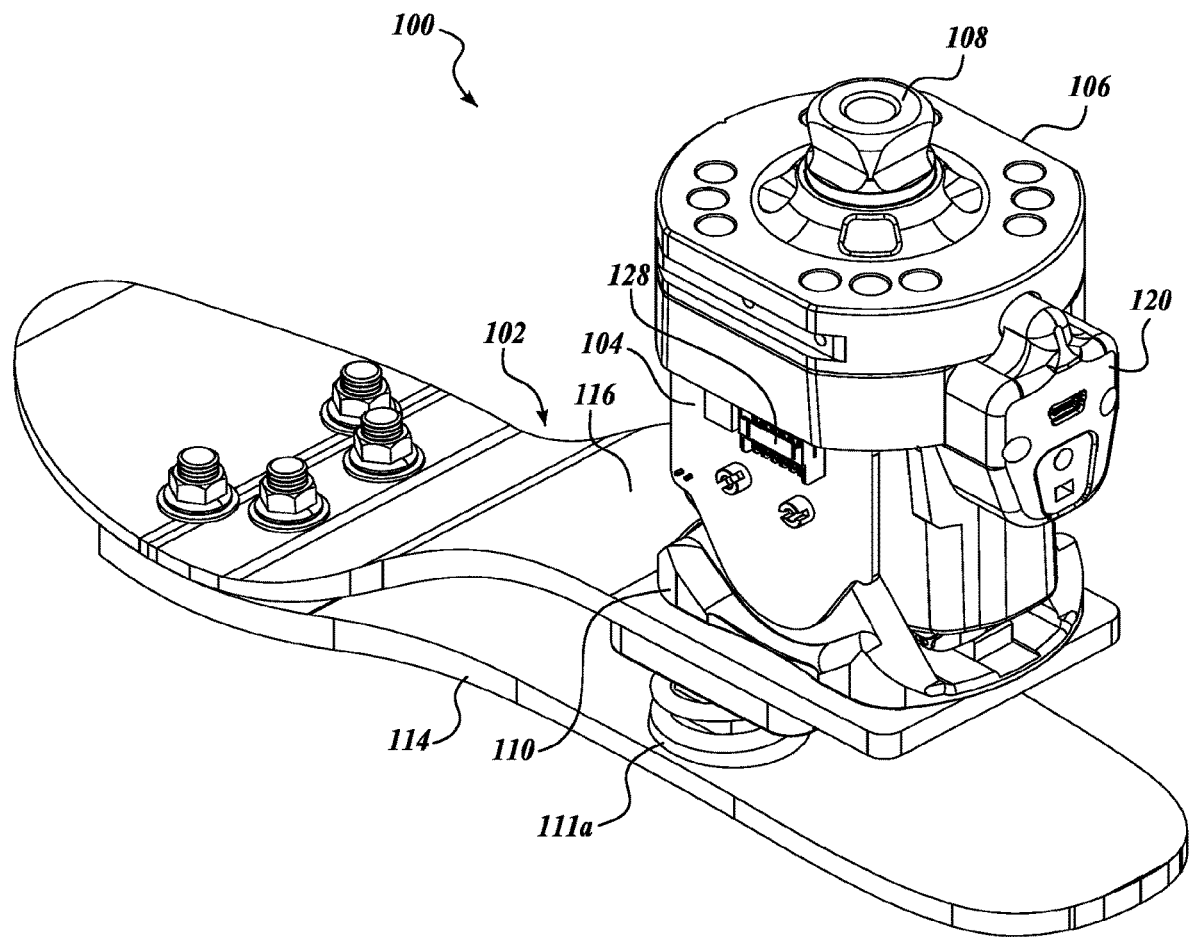
FIG. 1 is a diagrammatical illustration of a perspective view of a prosthetic foot and ankle joint with hydraulic actuators.

Referring to FIG. 1, an assembly 100 having a prosthetic foot 102 and ankle joint 104 with hydraulic actuators is illustrated. The assembly 100 further includes a transducer 106 coupled to the upper surface of the ankle joint 104. The ankle joint 104 or the transducer 106 may include one or more accelerometers, angle and temperature sensors, and strain gauges. The transducer includes an adaptor, such as a pyramid adaptor 108, to couple the assembly 100 to the bottom of a pylon (not shown). The pylon can be attached to a prosthesis socket that can receive an amputated limb. The transducer 106 is able to sense the moments acting between the bottom of the pylon and the ankle assembly 100. The moments at the interface between a prosthetic foot and the lower end of a pylon can be used to recognize various states of activity. Furthermore, the moments and forces at the interface between a prosthetic foot and the bottom of a pylon can be used to recognize states by comparison with moments and forces resulting from normal walking. In other words, deviations in the moments and forces from normal walking can predict other states, such as whether the ground slopes up or down, whether one is ascending or descending stairs, whether one is walking slow or fast, and other special situations. The ankle joint described herein is able to sense when deviations from normal walking occur and recognize the type of activity that is occurring and make adjustments to the ankle angle to better fit the activity.

In one embodiment, the moments can be described in a coordinate system comprising two orthogonal planes. One plane is the anterior/posterior (AP) plane, and the second plane is the right/left (RL) plane. The AP plane is the plane that is parallel to the longitudinal centerline of the foot 114, and the RL plane is orthogonal to the AP plane, and both intersect each other at the adaptor 108. A line passing vertically through the adaptor 108 can define the vertical axis. In one embodiment, the moment transducer 106 can be similar to the one described in U.S. Pat. No. 7,886,618, issued on Feb. 15, 2011, with changes as noted below. The '618 patent is fully incorporated herein in its entirety.

The transducer 106 can include a base 110. The base 110 has a center area which includes four beams projecting radially inward and upwardly to support the four sides of a pyramid adaptor 108. The pyramid adaptor 108 is used to connect many prostheses to pylons. The pyramid adaptor 108 allows two degrees of movement in the AP plane and in the RL plane to make angular adjustments between prosthesis components. Once an alignment is determined to be acceptable, set screws may be tightened against four sides of the pyramid adaptor 108 to fix the alignment at the desired angular positions in the AP plane and in the RL plane. The transducer can include sensors to measure the forces and moments. For example, in one embodiment, the transducer 106 can include a strain gauge on each of the two sides of each of four beams, wherein one beam is aligned in the AP plane posteriorly, one beam is aligned in the AP plane anteriorly, one beam is aligned in the RL plane medially, and one beam is aligned in the RL plane laterally. Four strain gauges can be configured into a Wheatstone bridge to measure moments occurring at the AP plane, and four strain gauges can be arranged into a second Wheatstone bridge to measure moments in the RL plane.

The ankle joint 104 with hydraulic actuators is attached via the base 110 to the upper surface of a prosthetic foot 102. The foot 102 can be any well known prosthetic foot. The ankle joint to foot connection utilizes a universal attachment allowing any one of various prosthetic feet to be used. Use of a two inch bolt pattern can allow a prosthetist some discretion in fitting a preferred energy storage keel.

In one embodiment, the foot 102 includes a lower sole section 114, and an upper foot section 116. The anterior portion of the sole 114 and the upper 116 can be connected at an anterior position, such as by screw fasteners. The sole 114 is configured generally flat, but may include an upward curve so as to mimic a foot arch. The upper 116 includes a flat member also including curves, such that the shape may be defined as being almost an "S" with soft curves when viewed from the side. The sole 114 and the upper 116 are separated at the heel or posterior portion. A set of springs 111a and 111b may be positioned between the upper surface of the sole 114 and the lower surface of the upper 116. The foot 102 may be covered in a rubber or plastic form resembling a human foot. Suitable materials include, but are not limited to, polyurethane.

The ankle joint includes a control box 120, which receives data from the transducer 106 used in control of the hydraulic actuators of the ankle joint 104. The ankle joint may include wireless communication to communicate with a controller operated from a personal digital assistant (PDA), or any other computer.

Figure 2:
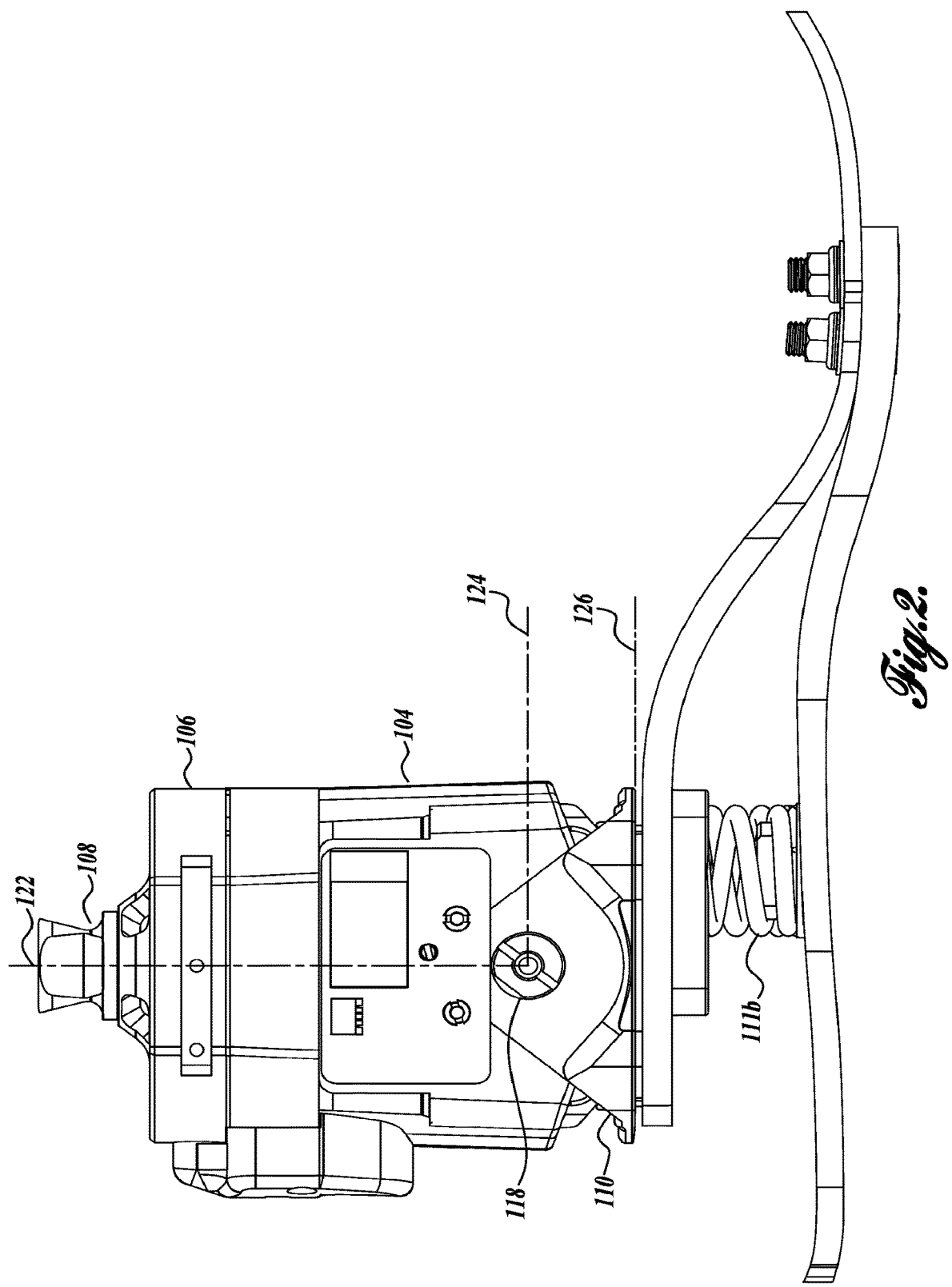
FIG. 2 is a diagrammatical illustration of a side view of the prosthetic foot and ankle joint with hydraulic actuators of FIG. 1.
Figure 3:
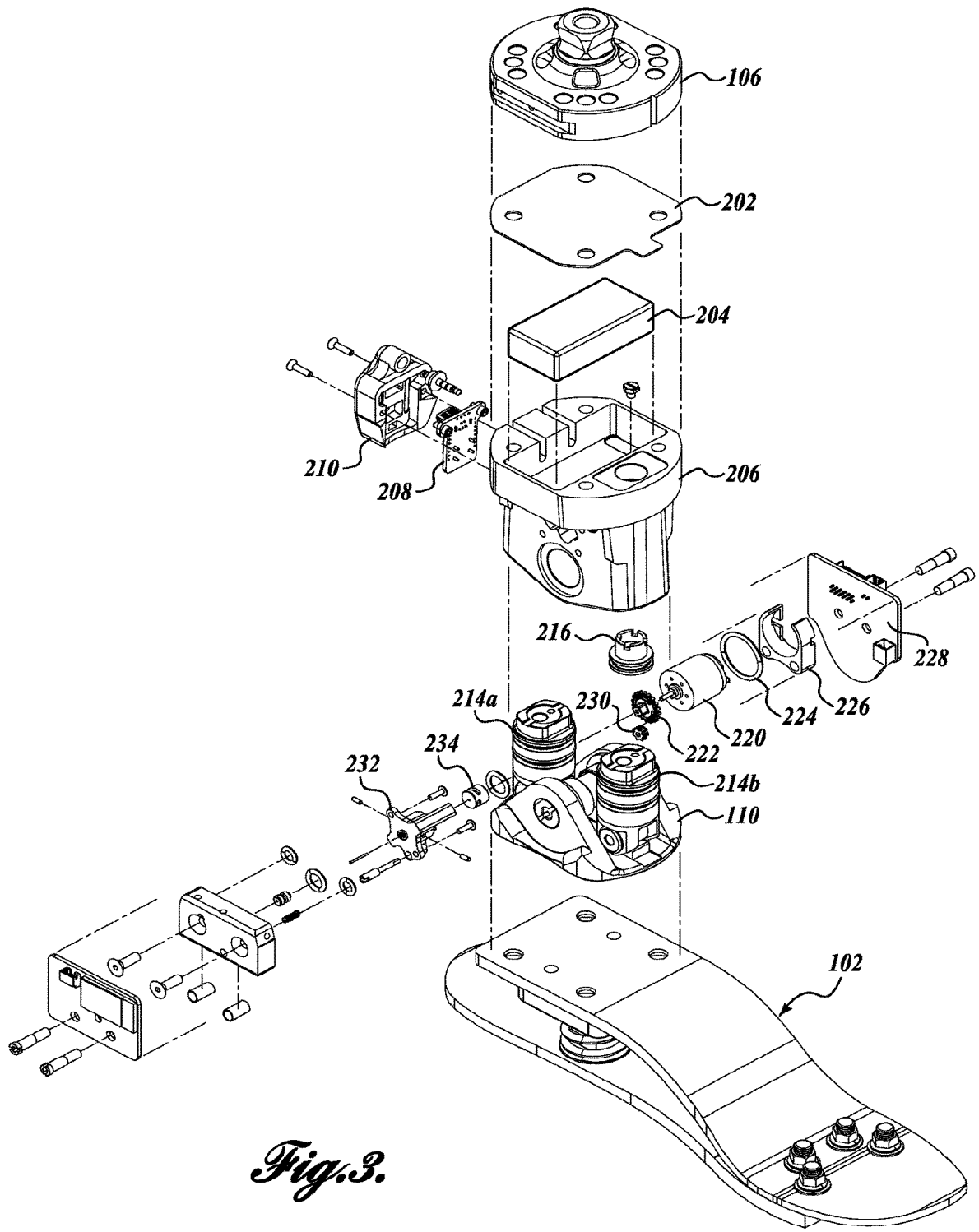
FIG. 3 is a diagrammatical illustration of an exploded view of the prosthetic foot and ankle joint with hydraulic actuators of FIG. 1.
Figure 4:
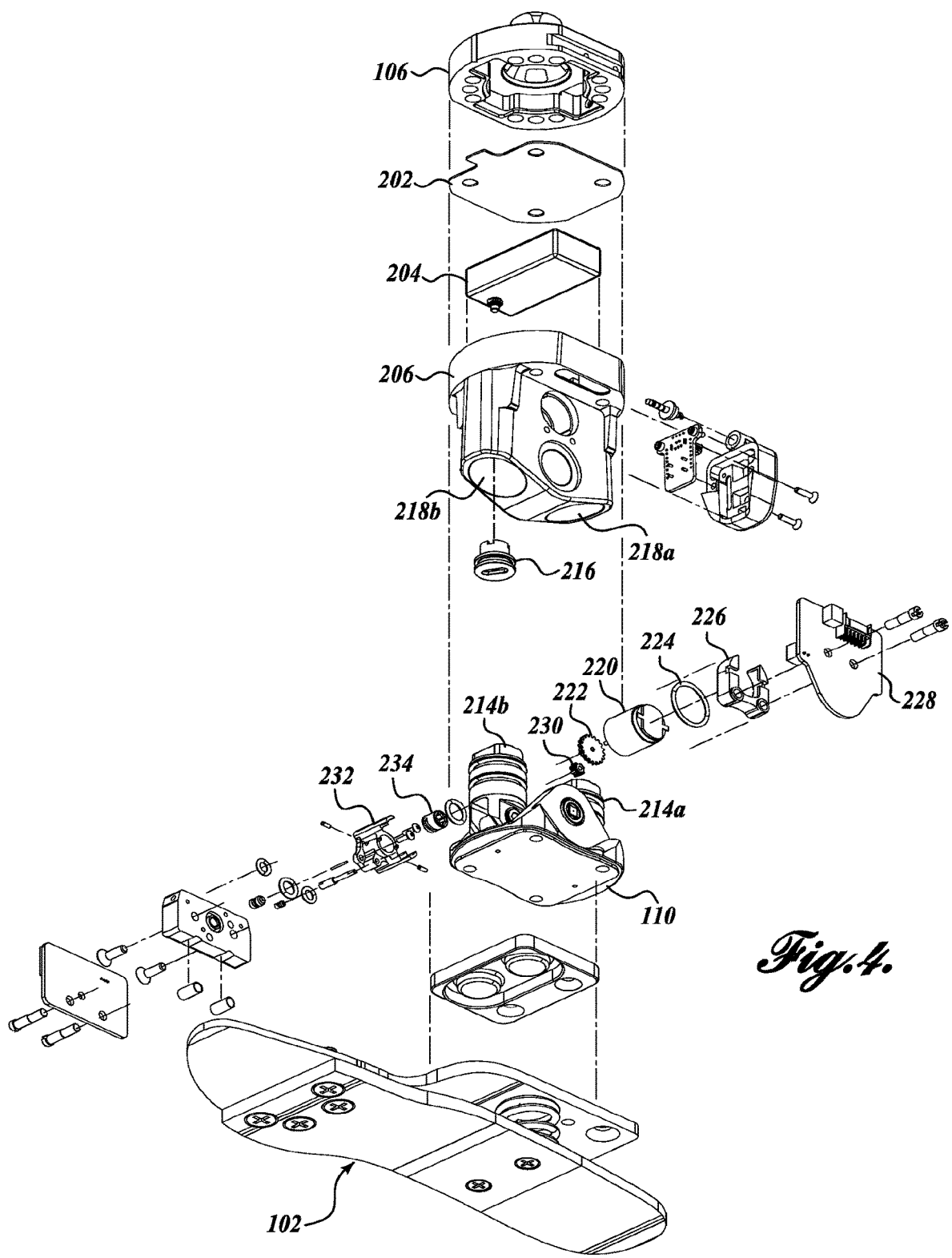
FIG. 4 is a diagrammatical illustration of an exploded view of the prosthetic foot and ankle joint with hydraulic actuators of FIG. 1.
Figure 5:
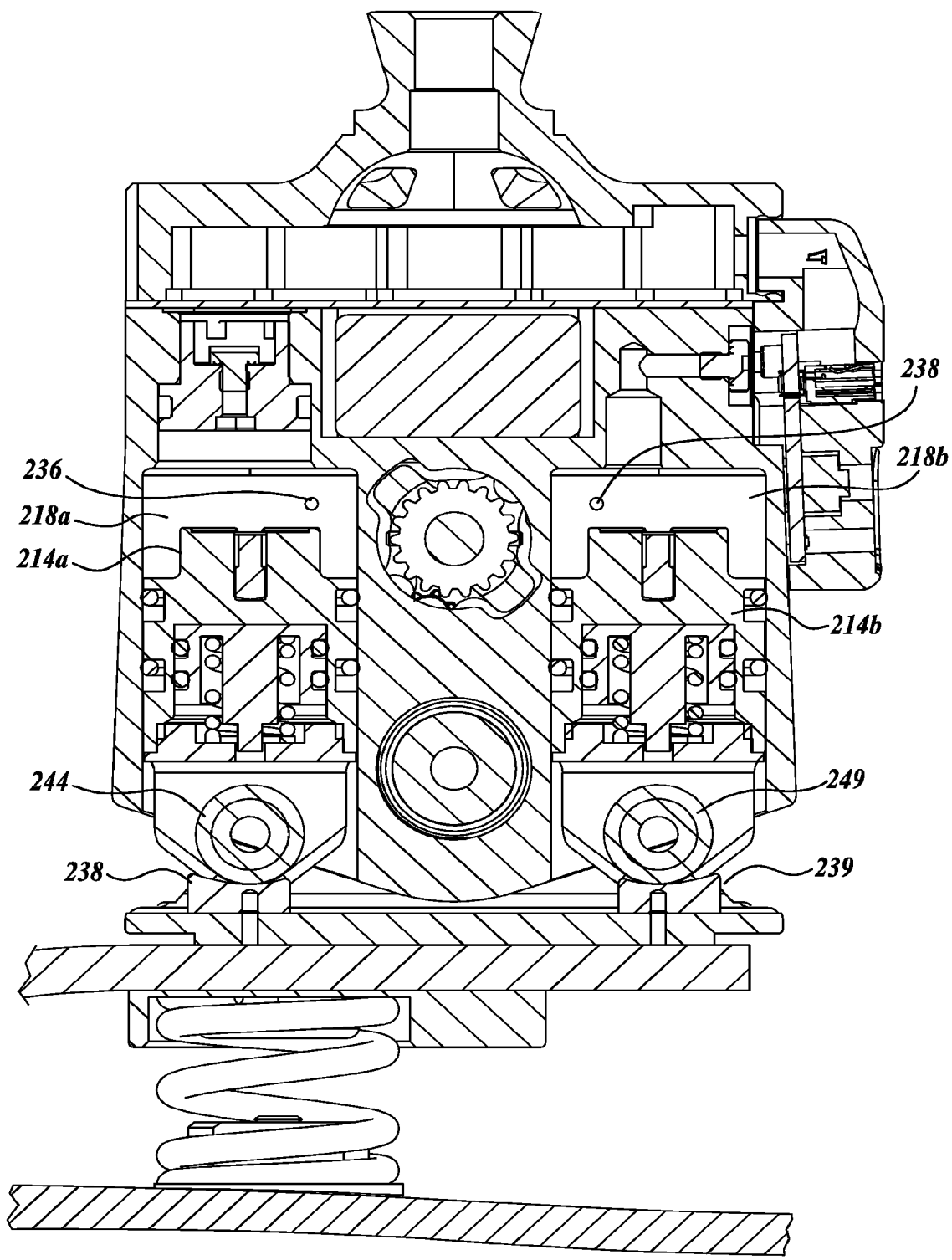
FIG. 5 is a diagrammatical illustration of a cross-sectional view of the prosthetic foot and ankle joint with hydraulic actuators of FIG. 1.

As shown more clearly in FIG. 2, the ankle joint 104 includes a pivoting axis 118. The pivoting axis 118 is at a connection point between the base 110 and the ankle joint body 104. The ankle joint 104 pivots at the pivoting axis to change the angle the foot 114 makes with any prosthesis connect to the top of the ankle joint 104. The ankle joint 104 includes a hydraulic dual piston arrangement. First and second pistons are positioned anteriorly, and posteriorly to the pivot axis 118. Both pistons can be in line with the AP plane. Each piston fits within a cylinder. The hydraulic fluid is transferred between cylinders. As described further below, the movement of hydraulic fluid between pistons may determine an angle between the ankle joint 104 and the foot 102.

The pivoting axis 118 is at the intersection of two lines 122 and 124. Line 122 is a line passing through the center of the ankle joint 104 and pyramid adaptor 108. Line 124 is a horizontal line passing through the pivoting point 118. The line 126 is parallel to line 124, which further describes a plane of the prosthetic foot 102. The hydraulic actuators, which are further described below, pivot the ankle joint 104 in a forward direction and in a backward direction along the AP plane to either increase or decrease the angle between lines 122 and line 124, which also corresponds to line 126. Lines 122 and 124 may also be viewed as defining planes. The line 124 is static, and consequently, line 126 is also static when the foot 102 is in a resting position, while line 122 is able to move forward to decrease the angle or move backward to increase the angle. This angle is commonly termed "plantarflexion." In accordance with one embodiment, the ankle joint 104 receives a variety of sensed inputs and is able to make determinations regarding the activity in which the patient is engaged. From the determinations, the ankle joint is able to provide an optimal plantarflexion angle to provide increased comfort, increased mobility, increased stability, and the like. Such decisions are made by using applied linear, fuzzy logic, neural net, or generic algorithms.

The ankle joint 104 and transducer 106 may first be used to collect a set of training data while the patient is engaged in a variety of activities (states or modes), wherein the plantarflexion angle can be varied for each training data set for each state. Initially, the plantarflexion angle can be determined based on best medical practices. The data set collected for the angle considered to be optimum for the state can then be used as the standard model of alignment. The model describes the preferred angle for a particular state. In use, when a state is determined, the ankle joint can be set to the model angle for that state.

From FIGS. 3-7, the construction of the ankle joint 104 and hydraulic system of one embodiment, may be understood. The ankle joint 104 body includes two cylinder bores 218a, 218b into which pistons 214a, 214b are placed. The first and second cylinder as well as the pistons are arranged such that the center axis of the first and second cylinders and pistons lie along the AP plane. The cylinders 218a, 218b are connected to each other through a series of channels 234, 236. A configuration of valves 232 are provided in the channels that control the flow of hydraulic fluid between cylinders, thereby the system maintains a constant system volume. The pistons can remain static and rigid by closure of the valves.

In one embodiment, the valves can be controlled through a motor 220. Motor 220 causes a drive gear 220 to rotate, which in turn drives a smaller gear 230. Gears 222, and 230 can be linked to valve arrangement 232. The valve arrangement is rotated to control the flow of fluid to the two cylinders 218a, and 218b. By rotating the valve stems, the hydraulic fluid can be directed to flow in one direction from either the cylinder 218a to 218b, or from 218b to 218a. The valve arrangement 232 can rest on a collar 234.

In one embodiment, the valves are solenoid valves that allow hydraulic fluid to pass through a piston or diaphragm from a high pressure side (the high side) to a lower pressure side (the low side). Solenoid valves can either be energized to open the valve or energized to close the valve. Alternative valves may include thermal valves, or other electromechanical valve. The closed loop hydraulic system includes the pair of cylinders, the valve cavities and a system of hydraulic fluid channels. Closed loop means that the volume of hydraulic fluid in the system remains a constant volume and no other hydraulic fluid is brought into the system or removed from the system with the exception of accumulators to offset thermal expansion and leaks of hydraulic fluid.

First and second pistons 214a, 214b cooperate to change the plantarflexion angle by allowing hydraulic fluid to be transferred from one cylinder to the other thus pushing down on one piston. Hydraulic fluid is moved between cylinders when pressure is applied on a piston. For example, when the heel of the foot makes contact with the ground, the pressure on the posterior piston exceeds the pressure on the anterior piston, and hydraulic fluid can move from the posterior cylinder to the anterior cylinder, assuming a valve is set to allow such transfer. Conversely, before the foot leaves contact with the ground, the pressure on the anterior piston exceeds the pressure on the posterior piston, and fluid may be transferred from anterior to posterior cylinder, again assuming a valve is set into the correct position. When one cylinder is filled with hydraulic fluid, this causes the ankle joint to rise on the side of that cylinder, while at the same time, the opposite cylinder is emptied of hydraulic fluid causing the ankle joint to lower on the side of that cylinder. As is apparent, the filling and emptying of cylinders on opposite sides of the pivot axis may cause one side to be lower than the other side, thus, pivoting the ankle joint 104 and changing the plantarflexion angle. Depending on whether the foot experiences a posterior moment or anterior moment, the ankle can dorsiflex when anterior moment is greater than posterior moment, and plantarflex when posterior moment is greater than anterior moment, assuming the valves allow such movement.

Figure 6:
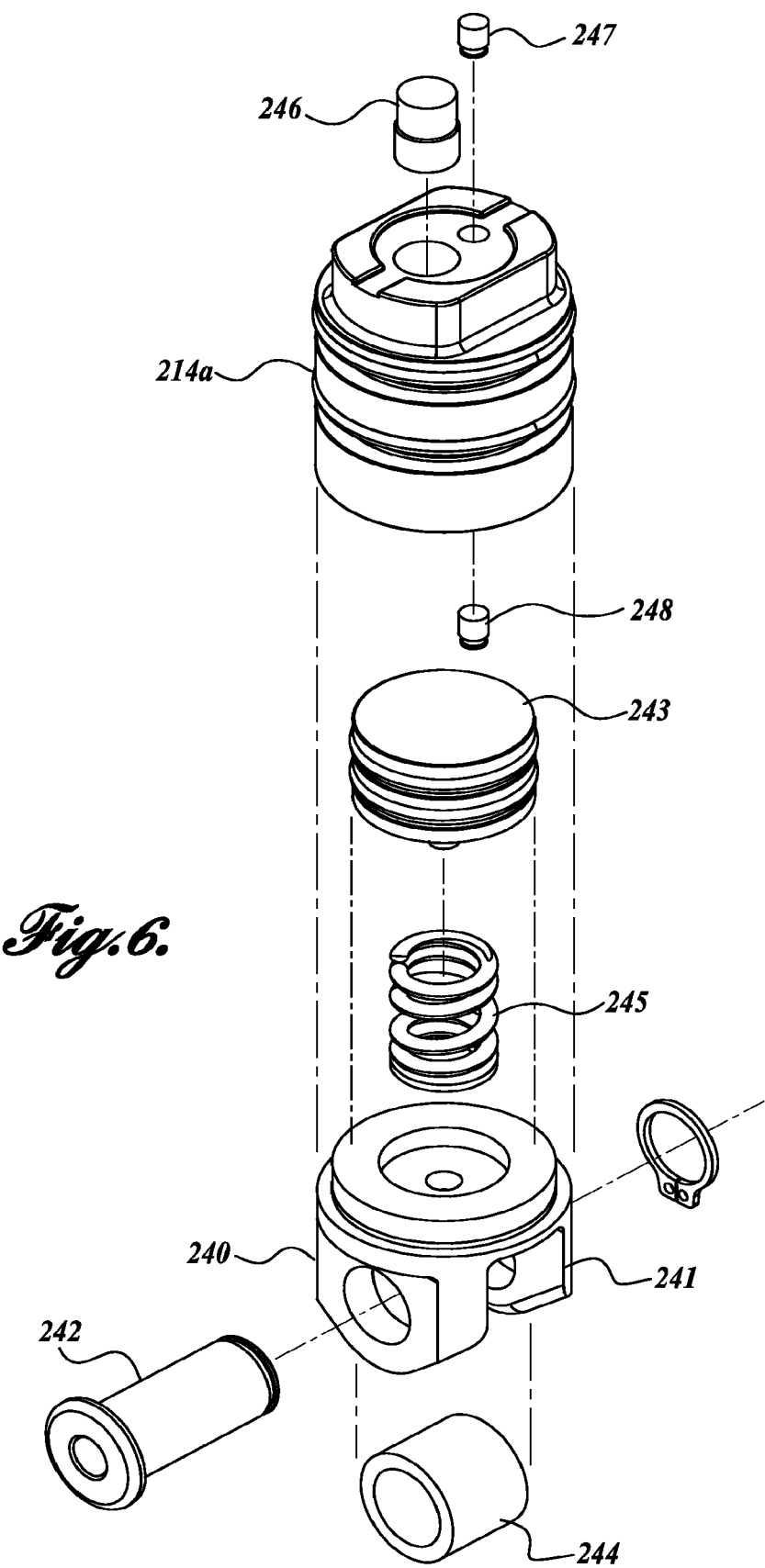
FIG. 6 is a diagrammatical illustration of an exploded view of an accumulator used in the prosthetic foot and ankle joint with hydraulic actuators of FIG. 1.
Figure 7:
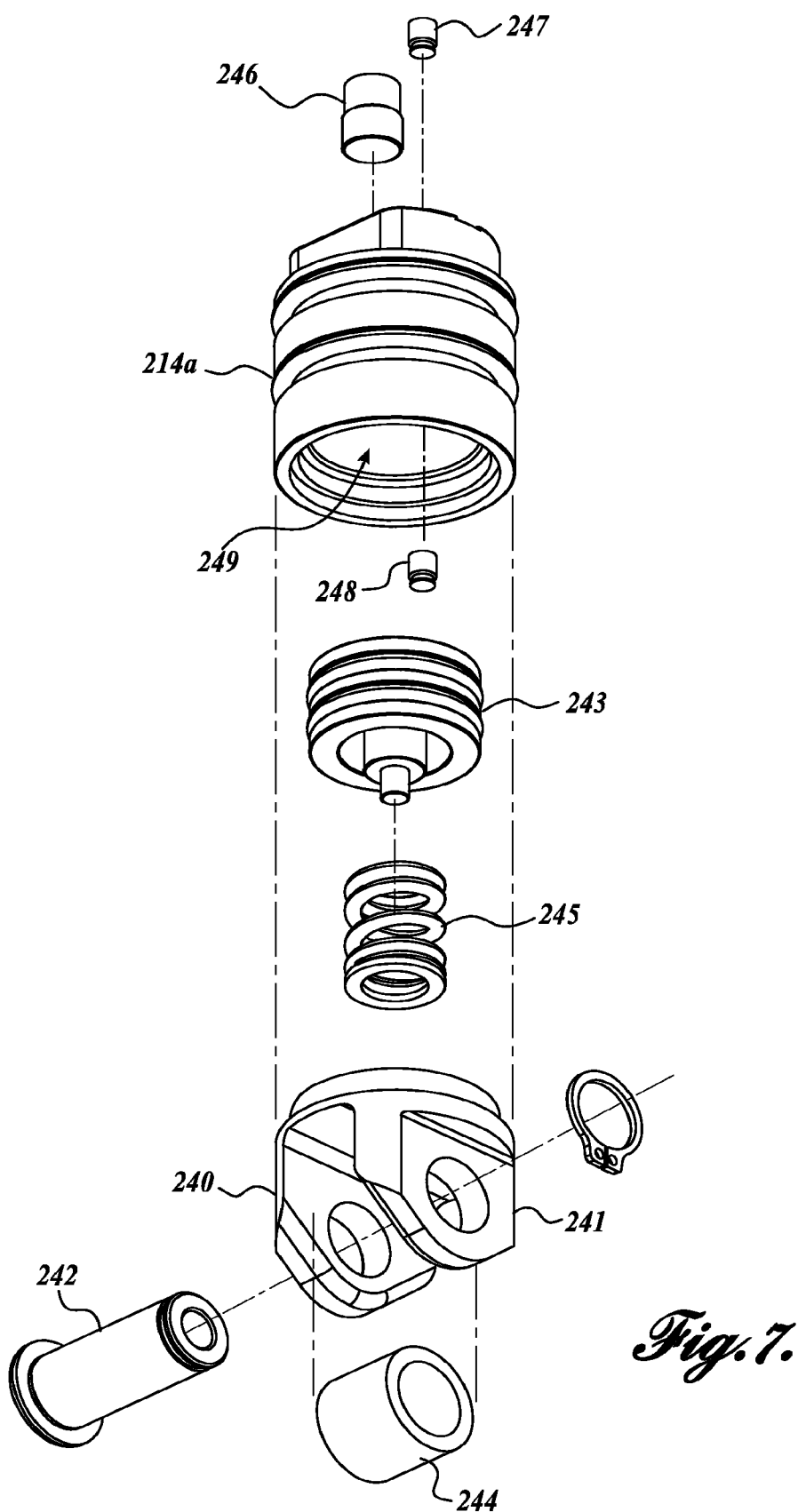
FIG. 7 is a diagrammatical illustration of an exploded view of an accumulator used in the prosthetic foot and ankle joint with hydraulic actuators of FIG. 1.

Referring to FIGS. 6, and 7, a detailed description of the piston 214a is provided. Piston 214b is similar to piston 214a, except for any changes specifically noted herein.

On the lower end (the distal or end facing the foot 102), the piston 214a may include a first and second vertical connecting rod 240, 241, and a horizontal shaft 242 and bearing 244 extending between the connecting rods 240, 241. The shaft 242 rides on, and faces the cam 238, which in turn rests on the base 110.

Also referring to FIGS. 6, and 7, an accumulator for piston 214a will be described. It is understood that a similar accumulator is provided in piston 124b, except for any changes specifically noted herein. The accumulator has an interior smaller subpiston 243 within a chamber 249 of the larger piston 214a. The subpiston 243 is forced up by a spring 245. Here, the spring 245 in the posterior accumulator exerts a greater force against subpiston 243, as compared with a spring in the anterior accumulator. This is because when the foot is in swing phase, hydraulic fluid is forced out of the posterior accumulator and into posterior cylinder 218a, which forces piston 214a down, causing ankle joint 104 to pivot the toe of the foot up, resulting in a force that pushes hydraulic fluid into the anterior accumulator because of the relatively weaker accumulator spring. This provides a toe-up bias on swing phase.

The accumulator includes a restrictor valve 246 and check valves 247, 248. The restrictor valve 246 regulates the amount of hydraulic fluid into the accumulator. The subpiston 243 provides temperature compensation by restricting flow to a slow flow rate rather than having angular movement "free" upon loading. An accumulator, in general, is a type of energy storage device. In this case, the accumulator stores and provides hydraulic fluid when a certain pressure is experienced in the main cylinder, i.e., 218a, 218b. For example, a piston under pressure 214a, 214b may first fill the accumulator before the piston 214a, 214b may experience movement. In one embodiment, a restrictor orifice or the use of a shear thickening fluid within the piston can provide temperature compensation. Flow is relieved through a one-way check valve 247 to keep the pistons in constant contact with cams. The toe (anterior) accumulator can be restricted at a different rate than the heel (posterior) accumulator to accommodate differences in gait pattern. This is because the heel moment is significantly less than the toe moment.

The shafts 244, 249 of pistons 214a, 214b rest on cams 238, 239, respectively, placed on the upper side of the bottom base 110, and face the pistons. The cams' upper surfaces form a parabolic shape. A parabolic shape is described by a curve whose points are equidistant from a focus point and directrix line. The axis of symmetry of a parabola passes through the focus point and the vertex point on the parabola. The shape of the upper cam surfaces can be described by a parabola whose vertex is at the middle of the upper cam surface. When the ankle joint 104 is level (forming a 90 degree angle), the piston shafts rest on the middle of the upper cam surface (i.e., the vertex of the parabola). When hydraulic fluid is added to a cylinder, the piston moving down may move inwardly on the cam surface, and when hydraulic fluid is removed from a cylinder, the piston moving up may move outwardly on the cam surface. The parabolic surface of the cams is advantageous in this respect as the parabolic shape defines a movement of the piston such that the force applied to the piston is parallel with the cylinder bore.

As can be appreciated, the load supported by the ankle joint 104 is transferred through the cam surfaces to the piston shafts and pistons causing a certain amount of pressure in the first and second cylinders 218a, 218b. The forces applied at the front and back of the ankle joint 104 are rarely if ever equal when used for walking, which means the pressures in the two cylinders are different. The uneven pressures can be used as the driving force to move the hydraulic fluid from one cylinder to the other. Further, the pressures inside the two cylinders can be measured using pressure sensors and used to calculate whether the ankle is in the proper plantarflexion angle or to detect and make corrections.

The cylinders 218a, 218b have an opening 236, 238, respectively, above the maximum reach of the pistons 214a, 214b. Hydraulic fluid fills the cylinders and is transferred into and out of the cylinder by channels. A valve may be constructed with a dual acting piston, meaning that one side of the valve piston is in communication with and sees the pressure of the first cylinder, and the other side of the valve piston is in communication with and sees the pressure in the second cylinder. The valve can be actuated to prevent hydraulic fluid movement, thus locking the pistons from moving within the cylinders, and the ankle joint 104 remains rigid and static. When the valve allows hydraulic fluid movement, the fluid flows from high to low pressure, and the ankle moves accordingly. For example, at heel contact, the posterior cylinder 218a experiences greater pressure from the anterior cylinder 218b. Therefore, if control valve is opened, piston 214a is compressed, forcing fluid out of cylinder 218a, and causing ankle 104 to plantarflex, increasing angle. On the other hand, before toe-off, the anterior cylinder 218b experiences greater pressure than the posterior cylinder 218a. Therefore, if a control valve is opened, piston 214b is compressed, forcing fluid out of cylinder 218b, and causing ankle 104 to dorsiflex, decreasing angle.

Figure 8:
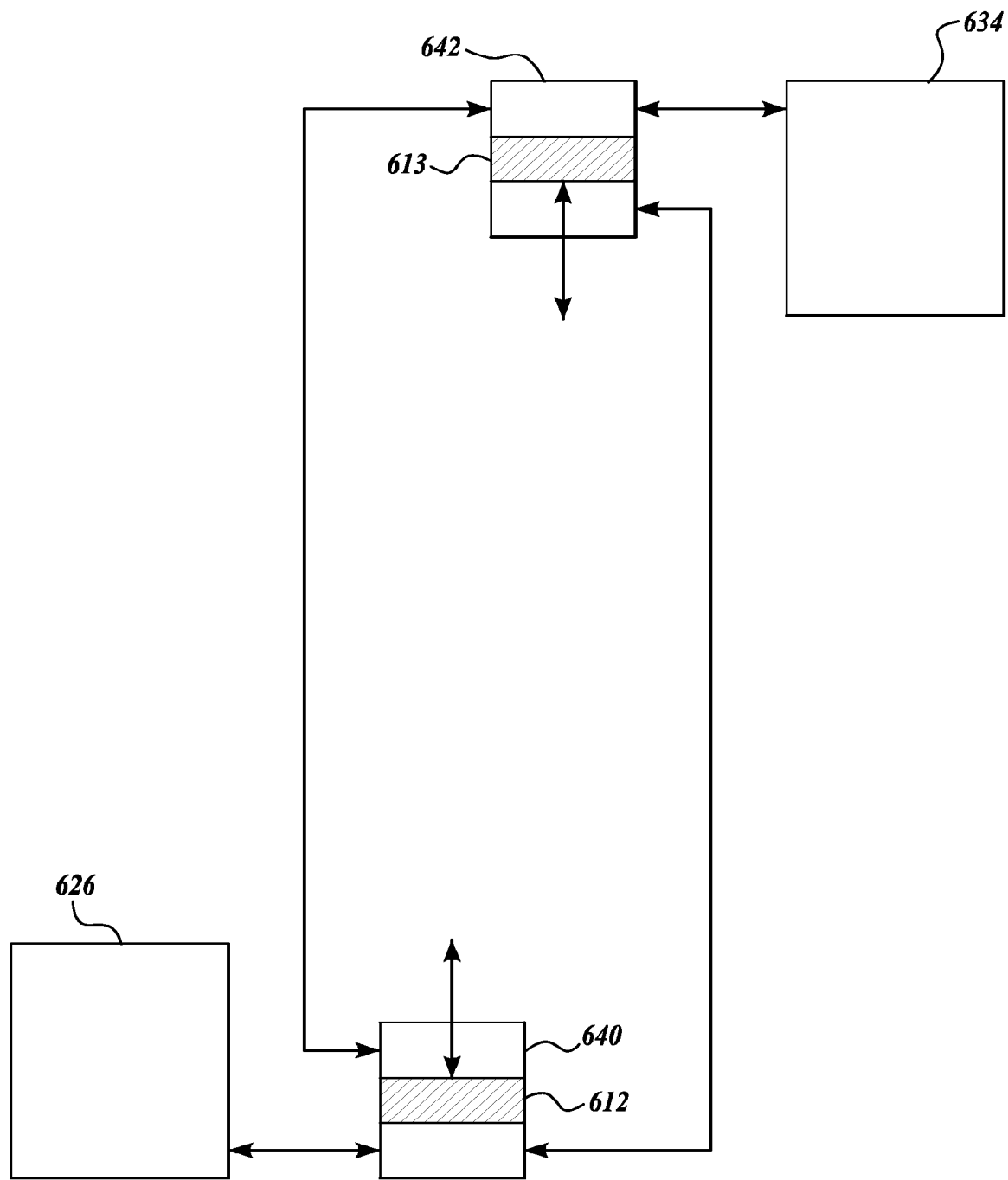
FIG. 8 is a schematic diagram of a hydraulic system used in the prosthetic foot and ankle joint with hydraulic actuators of FIG. 1.

A simplified schematic of a suitable hydraulic system for use in the ankle joint 104 is illustrated in FIG. 8. A first cylinder 626 connects to a high (pressure) side of a valve piston of a first valve 640 and also connects to the low (pressure) side of a valve piston of a second valve 642. The second cylinder 634 connects to the high side of a valve piston of the second valve 642 and also connects to the low side of the valve piston of the first valve 640. The valve pistons 612 and 613 may oscillate up and down as shown by the arrows to allow transfer of hydraulic fluid from the high side to the low side depending on which cylinder has the higher pressure. The pistons and cylinder come under repeated loads when the patient steps on the prosthesis foot. During this phase of walking, the pressure in the hydraulic systems can rise to over 2,000 pounds per square inch. This pressure provides the driving force for moving the hydraulic fluid from one cylinder to the other, thus, avoiding the need to have pumps to propel the hydraulic fluid through the system. The valves can be pulse shift valves that move in small increments. When the valves are not energized, the ankle joint 104 should be rigid, not allowing the transfer of hydraulic fluid into and out of any cylinder and/or valve. Each individual cylinder 626 and 634 may experience a different pressure when the ankle joint 104 is rigid.

Suitable valves for use in the hydraulic system may be solenoid valves. The solenoid includes an electrical contact. In one embodiment, a solenoid valve uses a piston or diaphragm to prevent the passage of fluid through the valve. The piston is held against a seat by equalizing both sides of the piston with the high pressure fluid. In one embodiment, when the solenoid is energized, the solenoid converts electrical current into magnetic force to move an armature. The armature allows fluid on the high pressure side of the piston to enter the low pressure side of the piston. The high pressure fluid can now push against the piston compressing a spring, thus allowing high pressure fluid to flow. The hydraulic systems are configured with two solenoid valves because either one of the cylinders may see high pressure. Depending on which cylinder has the high pressure determines which of the two valves to operate to allow transfer of the fluid. Normally, the second valve remains closed when the other valve opens.

Figure 9:
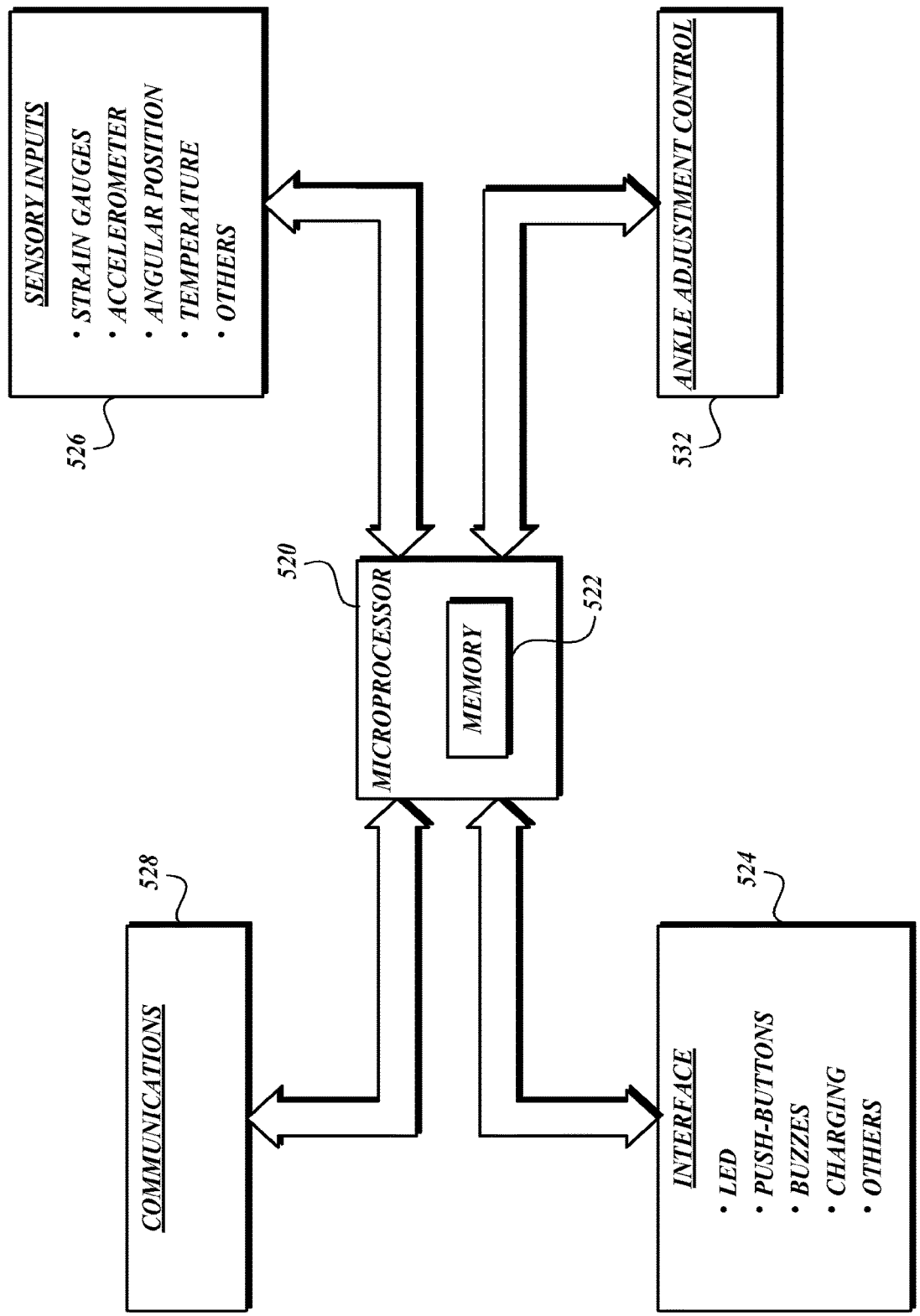
FIG. 9 is a schematic diagram of a sensing and processing system used in the prosthetic foot and ankle joint with hydraulic actuators of FIG. 1.

Referring to FIG. 9, a schematic diagram of the sensing and processing system of the ankle joint 104 is illustrated. The ankle joint 104 includes a microprocessor 520. The ankle joint 104 includes a power supply, such as a battery. The ankle joint includes a memory 522. The memory 522 may be used to store one or more algorithms that compares training data with real time data gathered from the sensors 526. The microprocessor 520 may communicate externally through a communication unit 528. Any communication unit capable of wireless or non wireless communication is suitable. In one embodiment, the ankle joint 104 may communicate with a mobile device. The ankle joint 104 may include an interface 524 to relay information. The microprocessor 520 receives inputs from various types of sensors 526, including, but not limited to, strain gauges, accelerometers, angle position sensors, temperature, and the like. The sensors 526 may be provided on a transducer, such as transducer 106, but other configurations are possible. Depending on the readings, the microprocessor determines the state of activity the patient is engaged in, whether the plantarflexion angle needs correction, and which valves to open to change the plantarflexion angle. The power supply powers the microprocessor 520 and also provides electrical current to operate the solenoid valves and the various angle, pressure or moment sensors 526.

The sensing and processing system of FIG. 9 provides an intelligent ankle joint that can respond to the environment through the use of sensory inputs. While a representative automated ankle joint is disclosed, it should be readily apparent that any similar mechanical ankle joint can be controlled in accordance with the methods disclosed herein. For example, any microprocessor-controlled ankle joint that can perform plantarflexion and dorsiflexion automatically can be instructed to perform in accordance with the methods disclosed herein.

Figure 10:
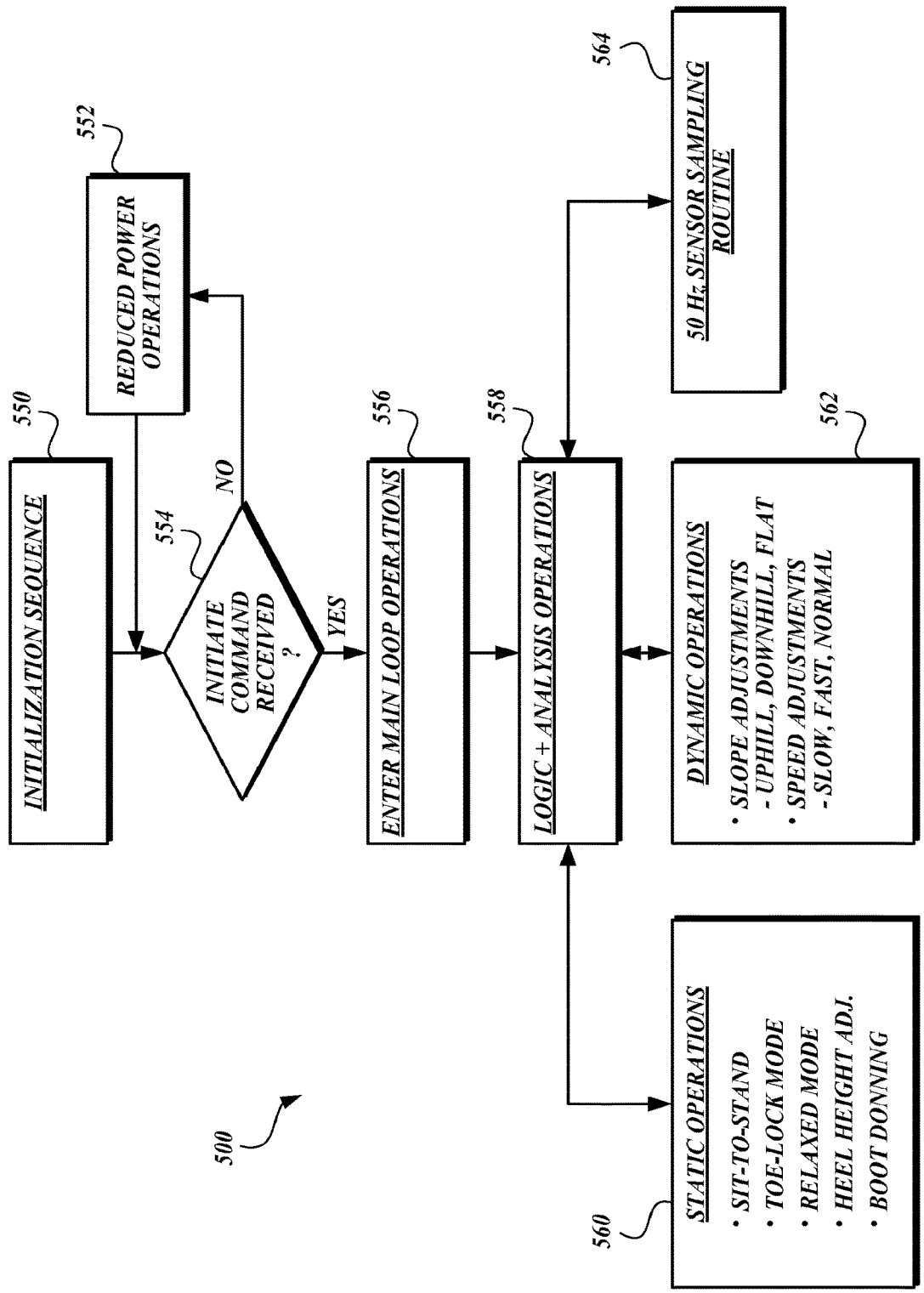
FIG. 10 is a flow diagram of the control scheme used in the prosthetic foot and ankle joint with hydraulic actuators of FIG. 1.

Referring to FIG. 10, a general overview of the ankle adjustment control scheme is illustrated.

In block 550, the sensing and processing system performs an initialization sequence. The initialization sequence may be started by the operation of a switch. The initialization sequence is to test the sensors and provide feedback on whether any sensors, a malfunction, or fault is detected with the ankle joint.

If the initialization sequence does not find a fault, the sensing and processing system continually checks whether any initiate command has been received. If no initiate command is received within a predetermined time limit, then, the sensing and processing system may enter into a reduced power operation mode. In reduced power operation mode, the sensing and processing system may shut down all power consumption, except for what is necessary to recognize an initiate command.

When an initiate command has been received, the process enters main loop operations, block 556. In main loop operations, the sensing and processing system may perform training of the sensing and processing system by gathering data specific to the patient. In one embodiment, training refers to the gathering of information using sensors 526 when the patient is walking at a normal gait and at a normal speed on a level surface. The information gathered from sensors 526 can be used to create a model that represents a normal gait. For example, a normal gait may be characterized by the AP and RL moments, the axial force, the number of strides over time, the duration of swing and stance phases, and the like. Upon initial use, the prosthetist may configure the device via a four step process. The initial step is to configure the neutral, vertical position. This is done by having the patient stand with normal stance and weight distribution and analyzing the gravity vector such that the accelerometer, and thus the main electronics of the device, can recognize the vertical orientation. This value may serve as the initial "home" position; that is to say, the default angular position from which all future changes can be made. However, in other embodiments, the "home" position may deviate from the vertical position.

The second step is dynamic prosthetic alignment performed in a manner consistent with best medical practice. In this step, the prosthetist aligns the prosthesis, including setting the ankle angle for normal walking.

The third step is to configure the device to the gait of the patient. This is done by zeroing the sensors (unloaded measurement), neutral weight measurement (patient standing still with even weight distribution), and capturing data for five consecutive strides of normal gait and speed for the patient, for example. These strides provide the data for decisions regarding when the patient is in a different state of ambulation (dynamic states), or whether there is ambulation occurring (static states).

The ankle joint 104 reads the main buffer for sensing various measurements. Such measurements can come directly from the transducer 106, if included, or from one or more accelerometers placed either on the transducer 106 or the ankle joint 104. The transducer can provide AP and RL moments and axial force, or any derivations thereof. The accelerometers can provide acceleration values in any one of six directions, i.e., along three axes.

As part of implementing method 500, the ankle joint 104 is trained to learn to distinguish the stance/swing phases during a normal walking gait of a particular patient, and also to recognize various weight and non-weight bearing states, such as sitting, standing, flat walking, uphill walking, downhill walking, stair ascending, stair descending, walking fast, walking slow, other special conditions, and the like, so that the ankle joint 104 can later recognize when such activity is occurring and adjust the plantarflexion angle most suited for the activity.

During training, and thereafter during use of the ankle joint, the ankle joint may receive or calculate one or more of the following variables, including, but not limited to, ankle angle (plantarflexion angle), axial force, stance duration, swing duration, stride duration, strides per minute, roll over percent (0 crossing for anterior/posterior (AP) moment), maximum AP moment (toe loading), minimum AP moment (heel loading), maximum AP moment percent (when the peak toe load occurred), minimum AP moment percent (when the peak heel load occurred), average slope (AP) from 30 to 50%, peak slope (AP) from 40 to 65%, maximum posterior moment, maximum anterior moment, maximum X acceleration, maximum X acceleration percent, maximum Y acceleration, maximum Y acceleration percent, maximum Z acceleration, maximum Z acceleration percent, maximum cumulative acceleration, maximum cumulative acceleration percent, minimum X acceleration, minimum X acceleration percent, minimum Y acceleration, minimum Y acceleration percent, minimum Z acceleration, minimum Z acceleration percent, minimum cumulative acceleration, minimum cumulative acceleration percent. Also, any calculated value using any of the above, such as an integral, an average, or a mean value, are also included as variables.

The fourth step is to enable or disable specific functionality and provide a mechanism to increase or decrease sensitivities or effects of each specific function (slope, speed, stair ascent and descent, and relax mode).

The sensing and processing system leaves the main loop operations when the configuration is complete and the prosthetist executes the "write" command to write parameters to the ankle.

When main loop operations are completed successfully, the sensing and processing system enters the logic and analysis operation mode, block 558. The sensory and processing system can evaluate data gathered from a variety of sensory inputs including, but not limited to, strain gauges, accelerometers, angular position sensors, temperature sensors, and the like, to make applicable judgments regarding gait, speed, slope, use of different footwear, and other predetermined, special conditions. Under such evaluations, the system has the ability to make adjustments to the angular rotation of the ankle to accommodate for the evaluated conditions.

In the logic and analysis operation mode, the logic and analysis operations include sampling the sensors, for example, at a rate of 50 Hz. The logic and analysis operations include determining whether a dynamic state is occurring and making adjustments to the ankle angle based on the determination. The dynamic states include making ankle angle adjustments based on a determination that the patient is walking uphill, downhill, walk slowly, walking fast, or normal, and ascending or descending stairs.

The logic and analysis operations include static states for making automatic ankle adjustments. The static states include a sit-to-stand state, a toe lock state, a relaxed state, a heel height adjustment state, and a boot donning state. Ankle adjustments are made based on a determination that one of these states is detected.

Figure 11:
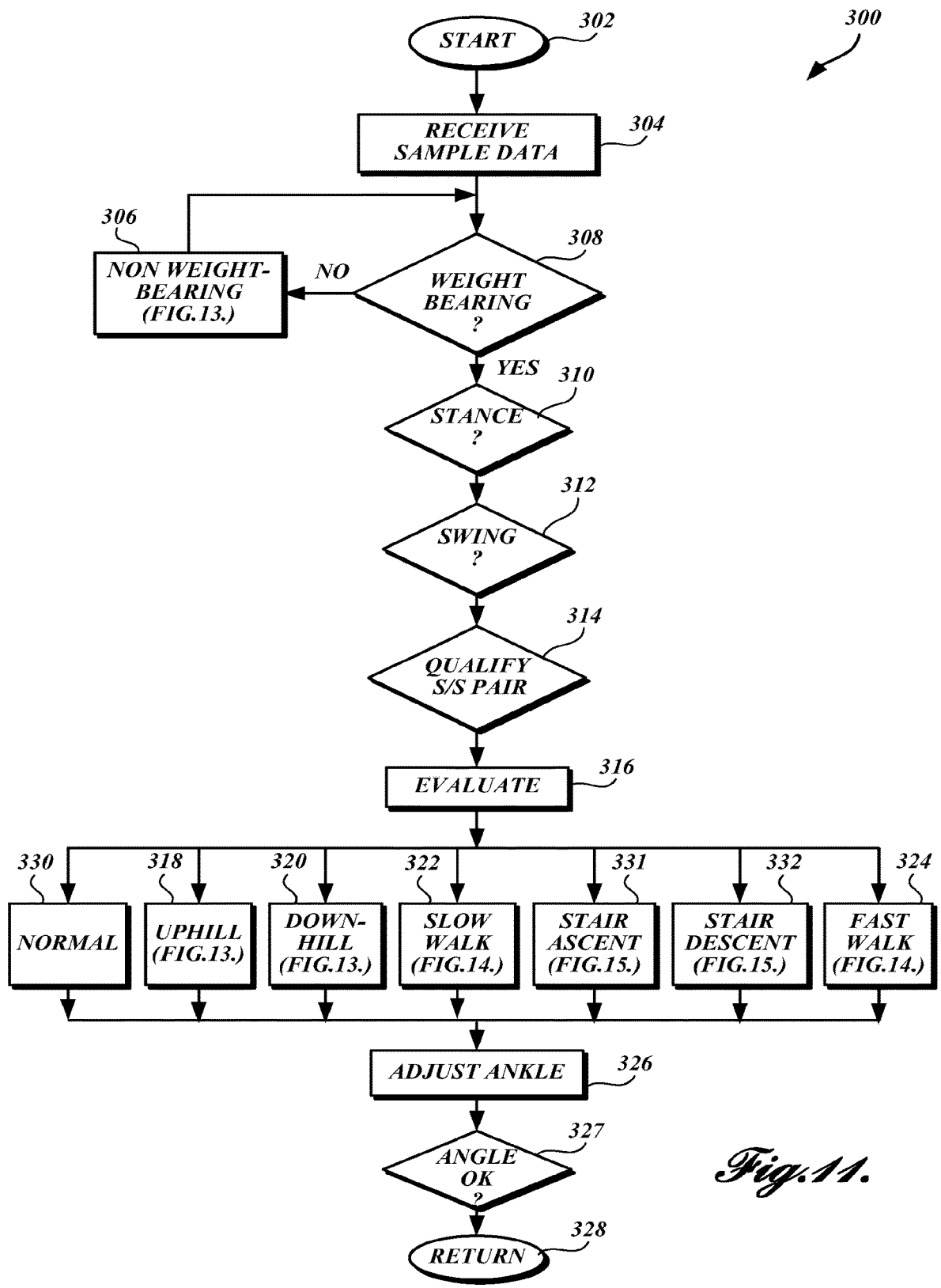
FIG. 11 is a flow diagram of the control scheme used in the prosthetic foot and ankle joint with hydraulic actuators of FIG. 1.

Referring to FIG. 11, a flow diagram of the logic and analysis process is illustrated. The logic and analysis process is performed after training data is collected, which may be stored in memory. A model of a normal gait with the corresponding optimal ankle angle may also be stored in memory, as well as any other models that are not a normal gait, such as uphill walking, downhill walking, slow walking, fast walking, ascending stairs, and descending stairs, with the corresponding angles. A normal gait is a gait when a patient walks with an optimally angled ankle (as decided by a prosthetist, for example) on a level surface, at a pace that is the most natural for the patient. Also, algorithms that determine plantarflexion angle of the ankle for each state are also stored in memory. Finally, the logic and analysis process is performed to assist the patient during his/her normal day, not in a clinical setting. For example, the process is performed as the patient carries on with his/her normal day to facilitate and assist in various activities. The process 300 begins at start block 302. From start block 302, the process receives sample data, block 304. Block 304 may receive moment data from strain gauges, such data is converted to represent forces and moments acting parallel to the anterior/posterior plane, parallel to the lateral/medial plane, and the force in the axial direction. From block 304, the process enters block 308.

Block 308 is for determining whether the ankle is weight bearing or not. In one embodiment, to determine whether the ankle is weight bearing, the axial force may be used. In the weight bearing determination block 308, if the amount of time that is considered to be weight bearing meets a specific temporal requirement, as well as other qualifying requirements, such as force levels, then that period of weight bearing may be deemed as a qualified stance phase, block 310. The force level can be some percent of the weight of the patient, for example. The process may proceed to determine whether a qualified swing phase has occurred, block 312. Block 312 is optional, and need not be performed. Block 310, and optionally block 312 are performed to determine whether the patient is walking normally. A normal gait includes each leg undergoing a stance phase and a swing phase. A stance phase is the period during which the foot is in any contact with the ground surface, while a swing phase is the period during which the foot is not in contact with the ground. In block 312, temporal and force requirements may be applied to determine the swing phase. Since in a swing phase, the foot is not in contact with the ground, the sensory and processing system determines whether the force level is below a threshold for a predetermined period of time. If the force level and time period meet the respective requirements, the sensing and processing system may then qualify a swing phase. In an alternative embodiment, the swing phase can be qualified first, followed by qualifying a stance phase. In either case, once the sensing and processing system has detected a qualified stance phase followed immediately by a qualified swing phase (or vice versa), such event may be deemed a qualified stance/swing pair, block 314. Alternatively, only the stance phase may be qualified in block 314. The system performs such evaluations to detect a normal gait.

Once a qualified stance/swing pair has been detected, the system may proceed to evaluate additional sensory data associated with the stance phase involved in the one or more qualified stance/swing pairs, or optionally just the stance phase or phases. From information gathered during one or more stance phases, the system can be able to determine the various states. Optionally, the system may also look to the swing phase or phases to determine states. Furthermore, a qualified stance/swing pair may also determine a dynamic state.

In one embodiment, determining a stance phase may include the use of axial load and the AP moment. For example, the axial load may go from minimum to maximum to minimum, and the AP moment (the moment in the AP plane) may trend from 0 to a posterior moment, then to anterior moment, and back to 0, thus indicating the end of a stance phase. In the swing phase, accelerometer parameters may be used. The system may calculate a swing phase when the axial force goes to less than 5% of the maximum axial force stored in the patient training data. Additionally, the system may also calculate a swing and stance pair when cumulative acceleration may be greater than 5% of the maximum cumulative acceleration, and there is a period of posterior moment and a period of anterior moment, and the total duration is less than 2 seconds. In one embodiment, the system may calculate the end of the swing phase when the cumulative acceleration is less than 5% of the maximum cumulative acceleration (such as using a moving average model), the axial force is greater than 5% of the maximum axial force stored in patient data, and the total duration of swing is less than 2 seconds. However, other parameters are possible.

In block 316, the system performs evaluations to determine a dynamic state using data gathered during the qualified stance phase. In some embodiments, the system may only use the qualified stance phase data, but, in other embodiments, the system may use both the qualified stance and swing phase data. In the evaluation block 316, the primary data analyzed during a qualified stance/swing pair analysis includes but is not limited to moment data. From this data, the system may extract specific parameters using the moment data, and determine the state. Based on the state, a corrective algorithm (command corrective ankle angle) may be performed. Such corrective algorithms may use a model of alignment that is constructed from training data. Such model represents the optimum plantarflexion angle for the determined state.

If a corrective action is deemed necessary, the microprocessor may command the valve that regulates the transfer of hydraulic fluid between cylinders, to open based on current AP moment to allow ankle motion in the correct direction and to close when the direction reverses. For example, posterior moment occurs when there is greater force on the heel of the foot than on the toe, and anterior moment occurs when there is greater force on the toe of the foot than on the heel. When there is posterior moment, the ankle angle can be adjusted to increase the plantarflexion angle. This is because force on the heel behind the pivot axis causes the foot to angle downward. When there is anterior moment, the ankle angle can be adjusted to decrease the plantarflexion angle (i.e., dorsiflex). While corrections to the plantarflexion angle can be performed during the stance phase, corrections to plantarflexion can also be performed during the swing phase.

The sensory and processing system uses as a reference, a coordinate system where the vertical axis of the transducer 106 is at the center, and as is conventional, points forward of the transducer axis are termed anterior, points to the rear of the transducer axis are termed posterior, points on either side are termed medial, or lateral. In one particular embodiment, the parameters that are calculated include the maximum anterior moment, maximum posterior moment, maximum medial moment, maximum lateral moment, and their respective instance (time) of occurrence, any averaged values, mean values, the stance duration, the anterior/posterior moment, zero crossing instance from a posterior moment to an anterior moment, and the slope of the anterior/posterior curve. During a stance phase, a continuous plot of the moments occurring in a plane that is aligned in the anterior posterior direction may generate a curve that initially registers a posterior moment at the initial contact of the heel with the ground. The posterior moment reaches a maximum, and before the middle of the stance phase is reached, the posterior moment is zero, and then an anterior moment begins to be registered. The anterior moment reaches a maximum after the middle of the stance phase, and then drops to zero at the end of the stance phase, or moment of toe off the ground. The "anterior/posterior" moment refers to the entirety of such curve, or any one or more points on such curve. Posterior moment refers to the portion of the curve (or any one or more points) where posterior moment is registered, i.e., from heel contact to the zero crossover point. Anterior moment refers to the portion of the curve (or any one or more points) from the zero crossover point to the toe-off. This curve is demonstrated, for example, in U.S. Pat. No. 7,886,618, FIG. 21, in a coordinate system where posterior moments are plotted below a horizontal reference line "0", and anterior moments are plotted above "0." However, the coordinate system can also be turned 90 degrees, "0" is merely an arbitrary selection.

During use, including the main loop operations, and the logic and analysis operations, the currently extracted and calculated parameters are compared to the parameters calculated during the training session in order to determine any variations in gait between the gait that is occurring in real time and the normal gait as determined in the training session. The sensory and processing system is capable of discriminating between various changes in gait from the normal, and attribute those changes to a change in slope, speed, ascending/descending stairs, or to some other event, such as the stopping of a weight bearing activity. To determine the variations that indicate a change in slope, speed, or other state, the parameters can be normalized to the training values, and the normalized values are the inputs for specific gait analysis algorithms described below.

As illustrated in FIG. 11, the evaluate block 316 may result in one or more determinations of walking normal, block 330, walking uphill, block 318, walking downhill, block 320, walking fast, block 324, walking slow, block 322, ascending stairs, block 331, or descending stairs, block 332. Once a determination is made of a particular state, algorithms determine if and how much to adjust the angle of the ankle in block 326. The system may perform a check in block 327 that the correct angle, as determined by an algorithm in block 326, is achieved.

Figure 13:
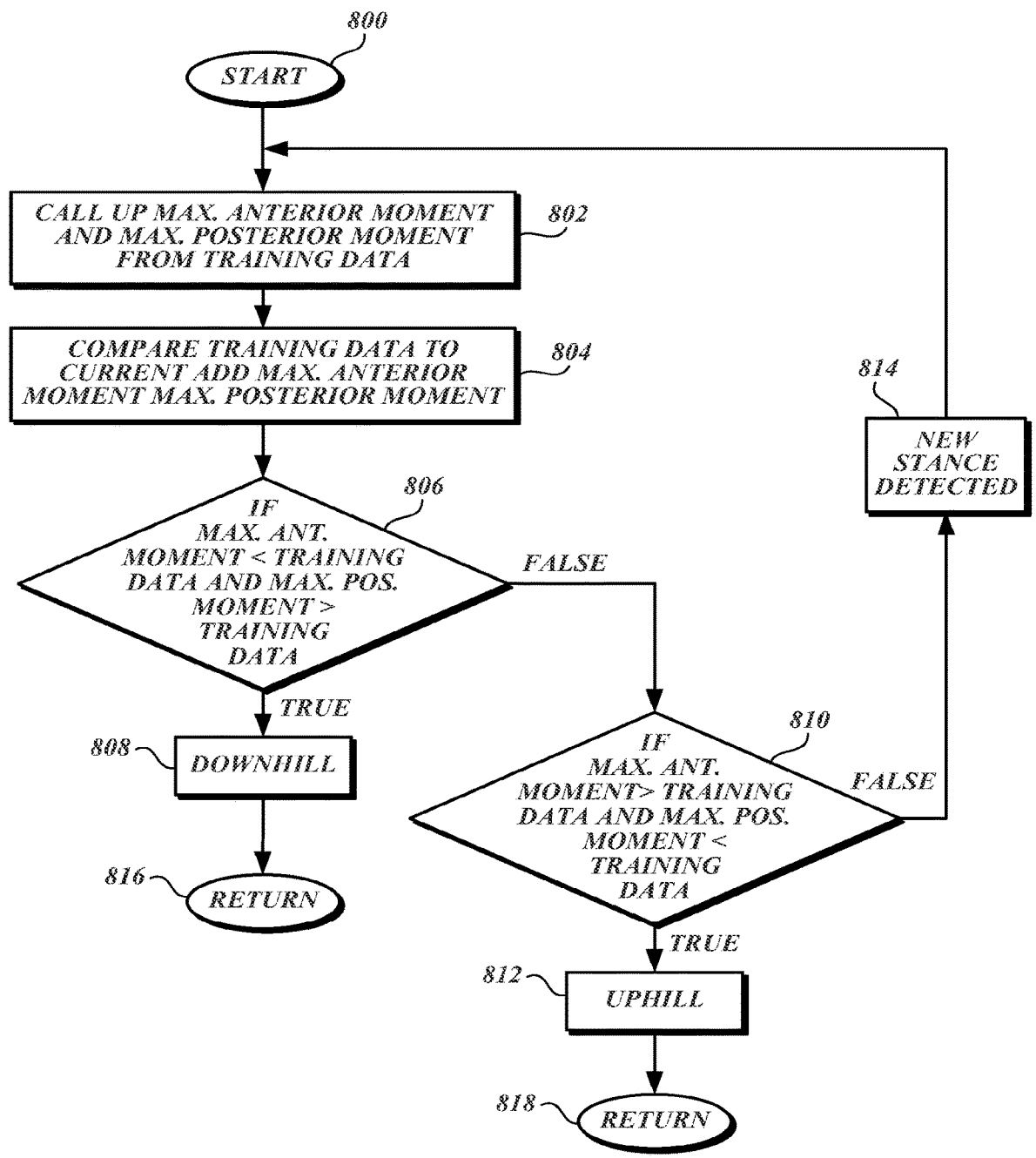
FIG. 13 is a flow diagram of the control scheme used in the prosthetic foot and ankle joint with hydraulic actuators of FIG. 1.

Methods for determining uphill walking and downhill walking are more thoroughly described in association with FIG. 13. Methods for determining walking fast and walking slowly are more thoroughly described in association with FIG. 14. Methods for determining ascending stairs and descending stairs are more thoroughly described in association with FIG. 15.

Normalization is a statistical method for negating a variable's effect on the data to allow comparisons of different sets of data by referencing the sets of data to a similar, or common scale. This is done by normalizing each key extracted parameter and calculating a predicted model value for each system state (upslope, downslope, stair ascent, etc. as applicable). These models were derived from a GMDH neural network model for characteristic patient gait. "Group Method of Data Handling," or GMDH refers to a number of algorithms used to predict or recognize patterns in multi-parametric datasets.

In one general implementation of analysis, the training process defines the typical relationship between maximum anterior moment and maximum posterior moment. Downhill gait may typically involve greater posterior moment and less anterior moment than a gait on level ground as the subject descends due to earlier and more prolonged posterior loading and shorter and less pronounced anterior moment. Uphill gait may involve greater anterior moment and less posterior moment. By calculating these relationships for each stance/swing pair and comparing them to a normal gait, the system can determine whether the patient is walking uphill or downhill and the severity of the slope. The ankle angle can be adjusted to return the relationship to normal or near normal (with normal defined as the relationship of posterior to anterior moment during flat level walking). For example, the angle is adjusted, then the anterior and posterior moments are compared to the anterior and posterior moments during normal gait. When the moments in real-time match the moments achieved while training, the ankle angle is considered to be optimum for the current situation. This implementation can be improved by evaluating other parameters to improve the false positive/false negative events.

There may also be algorithmic analysis to determine duration of stance and cadence (strides per unit of time), which indicate whether the patient is walking slowly or walking fast. Walking fast, or slow can be determined by detecting the duration of the stance phase as compared to the duration of the normal stance phase recorded during the training session, and/or, the time period between stance, and/or swing phases as compared to the time period between the stance and/or swing phases recorded during the training session. For example, when the duration of the stance phase is determined to be less than the duration of the stance phase during normal walking, the determination is reached that the patient is walking fast. On the other hand, when the duration of the stance phase is determined to be greater than the duration of the stance phase during normal walking, the determination is reached that the patient is walking slow.

Stair ascent or descent can be identified by evaluating axial load and the attenuation of anterior and posterior moment, in this case ankle angle would not be adjusted to normalize gait as this is not a "normal" gait pattern per se, but rather the ankle angle would be adjusted to enhance stability or reduce effort of ascent or descent.

The adjustments made to the ankle angle based upon the outcome of the determination of state may occur with the next stance phase, block 326. If an uphill condition is detected, block 318, the sensing and processing system may allow the ankle joint to dorsiflex a prescribed amount during the ensuing stance phases. If a downhill condition is detected, block 320, the system may allow the ankle to plantarflex a prescribed amount during the ensuing stance phases. The amount of angular change for uphill or downhill walking may be configured by the prosthetist in the initial setup of the device. For example, the ankle angle can move one degree in the predetermined direction as long as the condition is true. The change in the ankle angle in response to detecting uphill or downhill terrain can be cumulative; if the algorithm indicates that the patient is ascending a slope, a fixed amount of angular change is made (with this amount being configured by the prosthetist in the initial setup), and the patient's gait is analyzed again with the correction. The angle may also be increased or decreased depending on the magnitude of the variation. If the algorithmic inputs suggest the patient is still ascending the slope, an additional change can be made. The system repeatedly analyzes each stance and/or swing phase until the patient's gait is no longer indicative of slope ascent/descent thus suggesting their gait better matches a normal gait profile. Both the amount of change and the sensitivity to identification of a slope (a simple threshold value for comparison to the model output) are configurable by the prosthetist. In an alternative embodiment, the model identifies not only the presence of the slope but the predicted magnitude thereof and makes the full corrective adjustment in a single step.

If a walking slow condition is detected, block 322, the system may allow the ankle to dorsiflex a prescribed amount during the ensuing number of stance phases that occur within the qualified stance/swing pair cycle. If a walking fast condition is detected, block 324, the system may allow the ankle to plantarflex a prescribed amount during the ensuing stance phases. Speed-based variations may be a single change; i.e., the change in angle to the ankle joint occurs once regardless of the number of times the system identifies the patient is walking fast or slow.

Similarly, when a stair ascent or descent condition is detected, the change in the angular alignment of the ankle joint can be made in a single correction.

If a level walking surface and normal speed condition is detected, or in the absence of detecting any other condition, the system may set the ankle adjustment at the home position, i.e., the position of the ankle during normal gait as defined during the training session or as modified subsequently (and temporarily) by the patient to adjust to a change in footwear.

Any adjustments made due to analysis may result in the alteration to the home position generated upon initial training of the system. Effectively, a new home position may be created. This new home position may be the summation of the original home position and the appropriate offset required to facilitate the adjustment requested by the analysis. Therefore, if no offset is applied, the home position may remain as the original trained value.

In addition to making adjustments during a qualified stance phase or a stance/swing pair, the system may also perform operations depending on detection of other special case scenarios. The sensing and processing system is intelligent to determine states during non-weight bearing periods.

Figure 12:
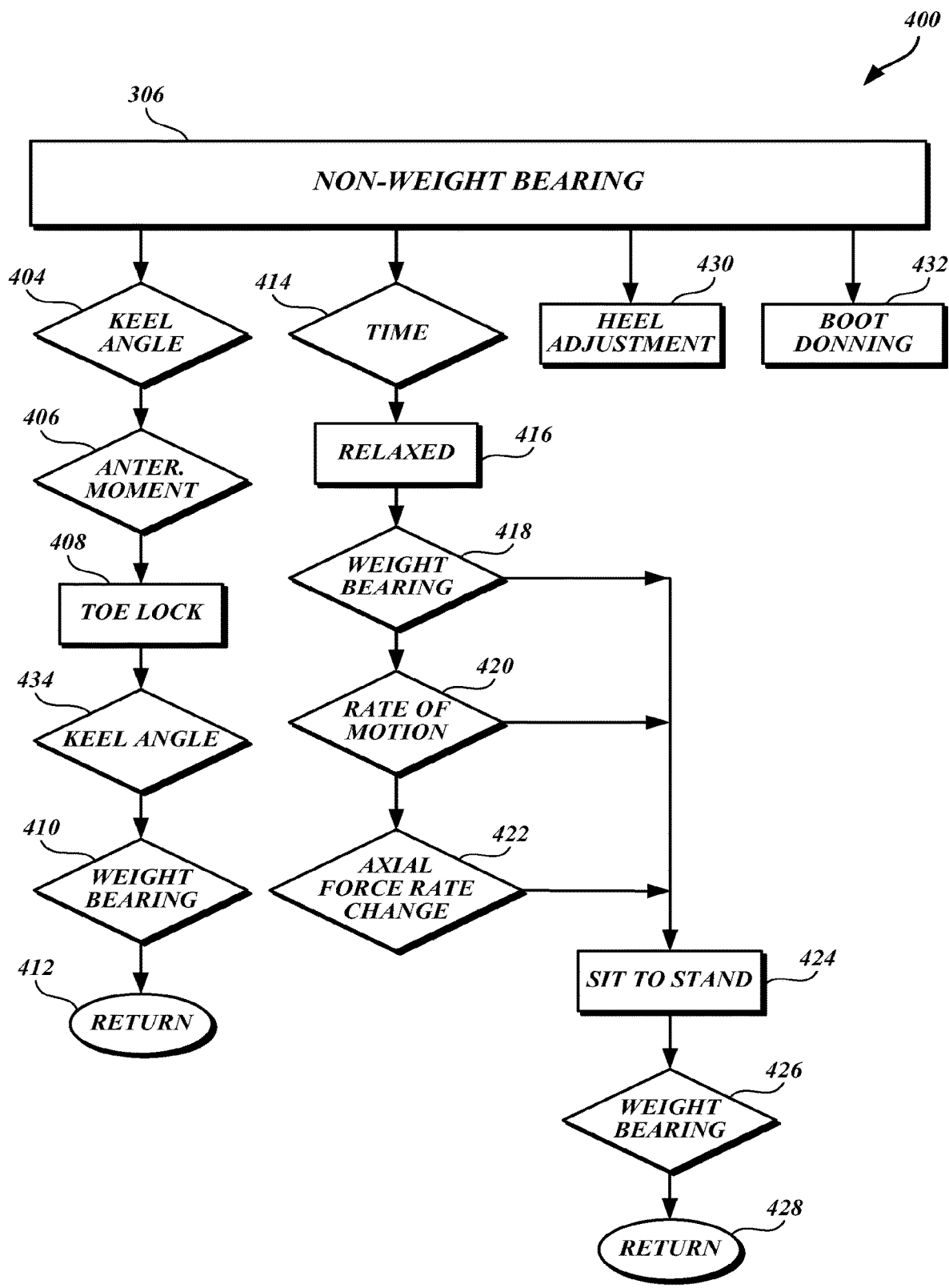
FIG. 12 is a flow diagram of the control scheme used in the prosthetic foot and ankle joint with hydraulic actuators of FIG. 1.

Returning to block 308, the sensing and processing system may determine when the ankle is not weight bearing, block 306, and the system may further perform analysis to detect special conditions of non-weight bearing states. Referring to FIG. 12, a schematic flow diagram of non-weight bearing modes are illustrated.

Non-weight bearing states may include, toe lock state (block 408), sit to stand state (block 424), heel adjustment state (block 430), and boot donning state (block 432).

A determination of toe lock results in the ankle joint being set rigid to avoid any angular movement. Toe lock condition is engaged if certain parameters are met. Preliminary to the analysis is a requirement that the sensing and processing system is detecting little to no weight according to block 306. Additionally, the keel angle must be greater than a predetermined value, block 404. In one embodiment, the keel angle is the angle defined by a true vertical axis and the pylon of the prosthesis. Generally, the keel angle is a description of the angle of the foot, or pylon, with the ground. The anterior moment value must be greater than a predefined value, block 406. An anterior moment correlates to a pressure being applied on the toe of the foot. The prosthetist can enter the predetermined keel angle and anterior moment thresholds. Both conditions can be sustained for at least two seconds, for example. The prosthetist may also make temporal adjustments. If both conditions are true for the predetermined time, the sensing and processing system enters the toe-lock state 408. In toe-lock state, the system may initially lock the ankle at its current position and allow movement towards its predetermined home position (the position during the training session during normal gait). The toe-lock exit conditions for toe-lock state include the keel angle being less than a predefined value, block 434, and the sensing and processing system is considered weight bearing (e.g., the patient is standing, for example), block 410. Both conditions should be met or exceeded for at least one second, for example. The prosthetist may set the predetermined keel angle and time to exit toe-lock. After the time has passed with both conditions met, the sensing and processing system may exit toe-lock state and proceed with its operations, such as returning to the continual checking for weight bearing and qualified stance/swing pairs. A scenario that is likely to trigger toe-lock state would be preparing to drive a vehicle. The patient could simply depress the brake pedal of the vehicle for at least two seconds, while in a sitting position, thereby meeting the pre-described entrance criteria for toe-lock state of a threshold keel angle, and time, and initiating the sequence that would lock the ankle angle in the current position, or at most, allow it to move towards its home position. Such a locked and constrained state would be desirable for operating a vehicle. To leave toe-lock state, the patient may exit the vehicle and stand (enter weight bearing state, and keel angle threshold) for at least one second, for example, in order to meet the toe-lock exit conditions and proceed with normal operations.

Relaxed mode occurs if the system is considered non-weight bearing, block 306, and not in toe lock mode for a defined amount of time, block 414. Once the system has entered relaxed mode, the ankle may be completely free to move, the extent of which being the maximum range of motion mechanically allowed by the ankle joint.

Sit-to-stand state, block 424, is entered if the system is first in the relaxed mode. Once the system enters relaxed mode, the system may then proceed to enter the sit-to-stand state if a set of parameters is met. These parameters include detection of weight bearing, block 418 (since to enter relaxed mode, the system must sustain a non-weight bearing condition for a period of time), and no qualified stance/swing pair is detected. Alternatively, the system enters the sit-to-stand state if the rate of motion (the rate of angular change of the ankle as measured by the angular position sensor) threshold is exceeded, block 420. A precondition, of course, is that the ankle is free to pivot. Alternatively, the system may enter the sit-to-stand state if the axial force rate of change threshold is met, block 422. Axial force is the force parallel to the pylon, for example. Determining weight bearing mode, block 418, can be a function of both axial force and/or on AP moment. For example, the system may measure the axial force when the AP moment indicates that the patient is in mid-stance, or the middle of the stance phase, so that the patient center of gravity is directly over the transducer. If the parameters are met or exceeded, after the relaxed mode, block 416, the system may allow the ankle angle to move towards the home position in the sit-to-stand state. So, if the ankle angle was adjusted while in relaxed mode, sit-to-stand may, in effect, allow the ankle to move back to its home position and remain fixed until an alteration is requested by entrance into any other state. For example, sit-to-stand is likely to occur when the patient proceeds from a sitting position, when the system has entered relaxed state, and the ankle has potentially moved, and continues into a weight-bearing activity, i.e., standing, walking, and the like. Under such a scenario, sit-to-stand state may effectively facilitate a smooth transition from sitting to a standing or walking state without the patient having to make any conscious effort to control the system. Accordingly, sit-to-stand state, block 424, is exited upon the system continuing to detect weight bearing, block 426, and a qualified stance/swing pair is detected. In such case, the system returns to block 308 and determination whether a stance/swing pair can be qualified.

The heel height adjustment state, block 430, may be implemented to allow for the use of different footwear by the patient. When different footwear is applied, the sensing and processing system can be reset to seek a new vertical position dependent upon the effective heel height added or removed by the application of the footwear. This vertical position may be defined as the static vertical angle of the pylon assuming that the sole of the foot or footwear is flat on the floor during this operation. The rotation of the ankle between those two reference points (the shank and the foot) can mean there is an extra degree of freedom. This new position may be saved as an offset from the original trained home position and may be maintained until another adjustment is called or, alternatively, upon reset of the device. Heel adjustment state, block 430, is entered via an external interface. This interface may be made by a prolonged button-push (for example, greater than 2 seconds) followed by a setup period for the patient, or by an external accessory such as a smartphone, computer, or Bluetooth-enabled watch or key fob. The amount of angular adjustment is determined by having the patient stand with equal weight bearing on both feet, and in a still position, and determining the new gravitational vector. This vector is offset by the original configuration by some amount due to the change in heel height and this deviation is applied to the "home" value as set by the prosthetist.

Therefore, with a heel height adjustment, a new home position may effectively have been created. Any other alterations requested due to algorithm results or any other state may act upon this new home position, which can be the summation of the original trained home position, and the offset applied by the heel height adjustment state.

The boot donning state, block 432, once invoked, may allow the ankle to enter free full range of motion. Boot Donning state is entered via an external interface. This interface may be by a prolonged button-push (for example, greater than 10 seconds) followed by a setup period for the patient, or by an external accessory such as a smartphone, computer, or Bluetooth-enabled watch or key fob. In such a state, the donning of a difficult to apply boot or other form of footwear may become a much easier process in that the ankle may be free to move in order to navigate into the footwear much more readily. Once accomplished, the ankle may move back into place by seeking its appropriate home position.

Referring to FIG. 13, a flow diagram of a method for determining whether a patient is walking uphill or downhill is illustrated. The method may be performed in the evaluation block 316 of FIG. 11.

The method starts in block 800. From start block 800, the method enters block 802. At this point, it is appreciated that the method has recognized a stance phase has occurred and has qualified the stance phase to be a true stance phase. In block 802, the processor may call up training data to calculate the maximum anterior moment and the maximum posterior moment from the training data. Alternatively, the maximum anterior moment and the maximum posterior moment may be calculated, and stored in a memory, and called upon when needed. As described above, training data is collected from the patient in order to recognize the various states of weight bearing and non-weight bearing states. To collect training data, the patient may be wearing the system while walking normally, climbing stairs, descending stairs, walking fast, or walking slow. This training data is used to prepare a representative trend of axial forces and/or AP and RL moments as the patient is engaged in any of these activities. Then, later when the patient is using the system, the system may learn to recognize trends and match the data occurring in real time with the training data and determine which activity the patient is engaged with. However, in other embodiments, the system is programmed to recognize deviations between the data occurring in real time and the training data collected when the patient is walking in a normal gait. These deviations predict whether the patient is engaged in one of the weight bearing and/or non-weight bearing states.

In one embodiment, the method may determine whether a patient is walking uphill or downhill by determining how the data collected in real time deviates from the data collected during a normal gait. One of the variables that is calculated during the data training session is the maximum anterior moment and the maximum posterior moment. As described above, walking generates a moment or bending force that is parallel to the AP plane during a stance phase. A stance phase is the period during which a foot is in contact with the ground. The stance phase has a beginning called the initial contact, and an end called the toe-off. If the moments in the AP plane are plotted in a coordinate system where posterior moments induced by heel contact are plotted below a reference (the "0" reference), and anterior moments induced by contact with the toe are plotted above the 0 reference, a plot of AP moments occurring during a stance phase may result wherein posterior moments occur at initial contact, followed by anterior moments to the end of toe-off. The point at which the anterior moment overcomes the posterior moment is termed the crossover point, and generally occurs before the middle of the stance phase is reached. The initial contact of the stance phase to the crossover point signifies a period where the posterior moment overrides the anterior moment, and the period from the crossover point to toe-off signifies a period where the anterior moment overrides the posterior moment. Each period of anterior and posterior moments has a maximum which is reached approximately at the center of each respective period. Moments in the AP plane apply forces to the prosthesis in a forward or backward direction.

In one embodiment, in order to determine whether a patient is walking uphill or walking downhill, the average or a mean of a plurality of maximum anterior moments and maximum posterior moments for a plurality of stance phases of the training data can be calculated. The average or mean maximum anterior moment and the maximum posterior moment can be stored in memory for later comparing to moments occurring in real time to determine whether the patient is walking uphill or downhill.

From block 802, the method enters block 804. In block 804, the system compares training data including the maximum anterior moment and the maximum posterior moment calculated from training data to current data collected in real time, such as in the course of the day. From block 804, the method enters block 806.

In block 806, a determination is made whether the maximum anterior moment is less than the maximum anterior moment evaluated from the training data, and also, a determination is made whether the maximum posterior moment is greater than the maximum posterior moment evaluated from the training data. If the conditions in block 806 are true, the method determines that the patient is walking downhill, block 808. If the conditions in block 806 are false, then, the method enters block 810 where a second determination can be made. In block 810, a determination is made whether the maximum anterior moment is greater than the maximum anterior moment evaluated from the training data and also whether the maximum posterior moment is less than the maximum posterior moment evaluated from the training data. If the conditions in block 810 are true, the system determines that the patient is walking uphill, block 812. If the conditions in block 810 are false, the method awaits the detection of a new stance, block 814, and repeats the evaluation process.

If a downhill condition is detected, block 808, or an uphill condition is detected, block 812, the method returns to FIG. 11, where an adjustment is made to the ankle in block 326.

It should be realized that the method illustrated in FIG. 13 is one embodiment for determining uphill or downhill walking, it is to be appreciated that other methods exist that may be substituted. For example, instead of comparing the maximum anterior moment and the maximum posterior moment with training data corresponding to a normal gait, the method can compare any variables to training data collected while the patient was actually walking uphill and walking downhill. In such a case, the system can determine uphill and downhill walking by recognizing the similarity of one or more variables to the training data collected during uphill and downhill walking.

Figure 14:
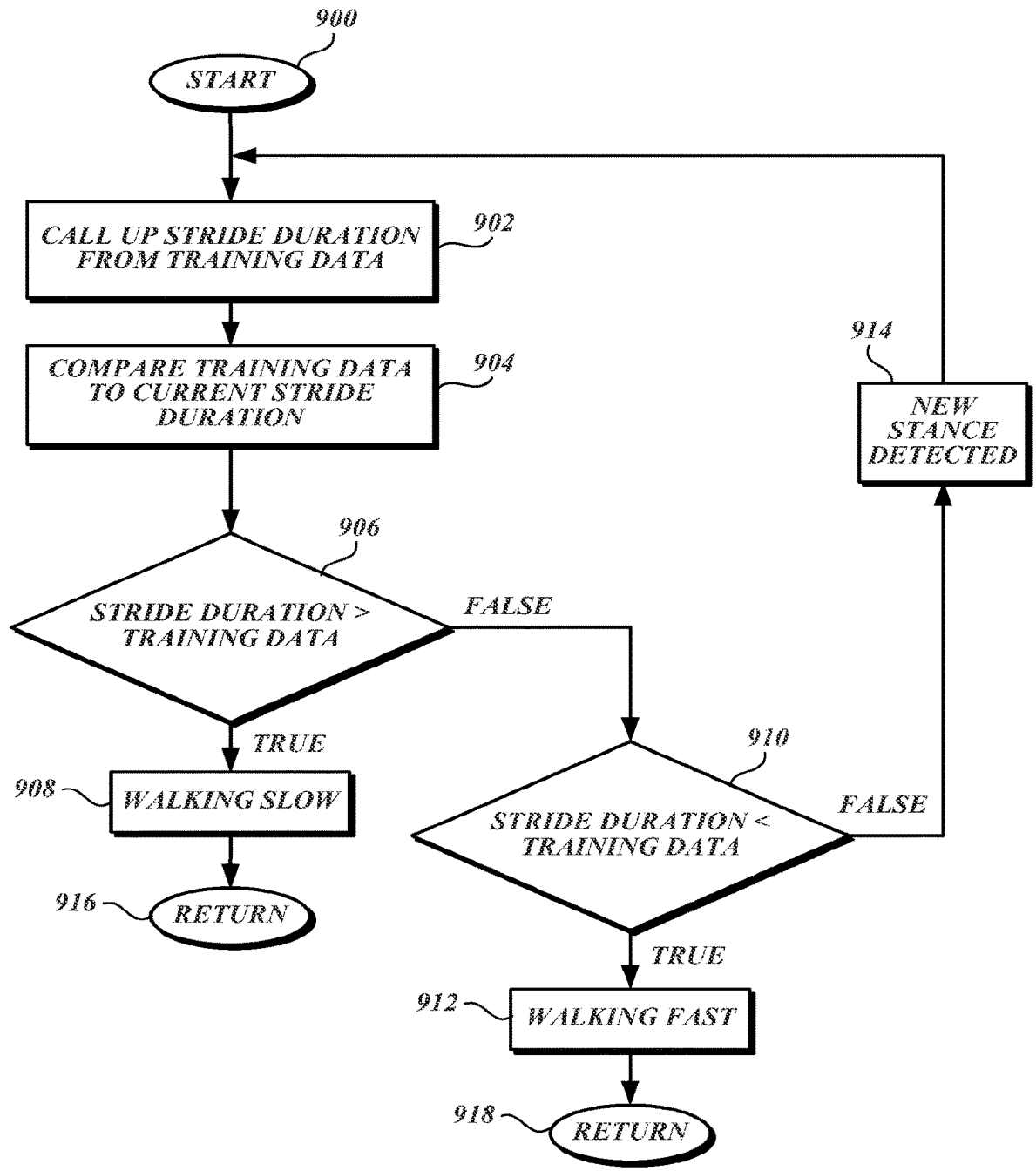
FIG. 14 is a flow diagram of the control scheme used in the prosthetic foot and ankle joint with hydraulic actuators of FIG. 1.

Referring to FIG. 14, a method for determining whether a patient is walking slow or walking fast is illustrated. The method may be performed in the evaluation block 316 of FIG. 11. The method starts with start block 900. At this point, it is appreciated that the method has recognized a stance phase has occurred and has qualified the stance phase to be a true stance phase. From start block 900, the method enters block 902. In block 902, the method calls up training data collected during normal walking. In particular, in one embodiment, the method may call up stride duration. Stride duration is the length as measured by time of completion of one complete cycle. For example, from initial contact to the next initial contact or from toe-off to the next toe-off, or even from mid-stance to the next mid-stance. It is to be appreciated that the time of one complete cycle can be averaged, or a mean taken from a plurality of stride sample times. A walking speed can also be detected by counting the number of strides per unit of time, such as, the number of strides per minute.

From block 902, the method enters block 904. In block 904, the method compares the training data of a variable that identifies a stride duration to a current stride duration variable occurring in real time. From block 904, the method enters block 906. In block 906, the method determines if the stride duration in real time is greater than the stride duration evaluated from the training data. If the condition in block 906 is true, real time stride duration is greater than stride duration of training data, the method determines that the patient is walking slowly, block 908. However, if the condition in block 906 is false, real time stride duration is not greater than stride duration of training data, the method enters block 910 and performs a second determination. In block 910, the method determines if the stride duration in real time is less than the stride duration evaluated using the training data. If the condition in block 910 is true, real time stride duration is less than stride duration of training data, the method determines that the patient is walking fast, block 912. If the determination in block 910 is false, the real time stride duration is not less than the stride duration evaluated from the training data, the method awaits the detection of a new stance, block 914, and repeats the evaluation process. After detecting a walking slow condition, block 908, or a walking fast condition, block 912, the method returns to FIG. 11, where the next step in the overall method is adjustment of the ankle angle, block 326.

It should be appreciated that the method illustrated in FIG. 14 is one embodiment of determining a walking slow and a walking fast condition using the stride duration as the measured variable. However, other variables are possible, such as the number of stances over a given time period or the number of swing phases over a given time period or, for that matter, the cadence, such as stances per a unit of time.

Figure 15:
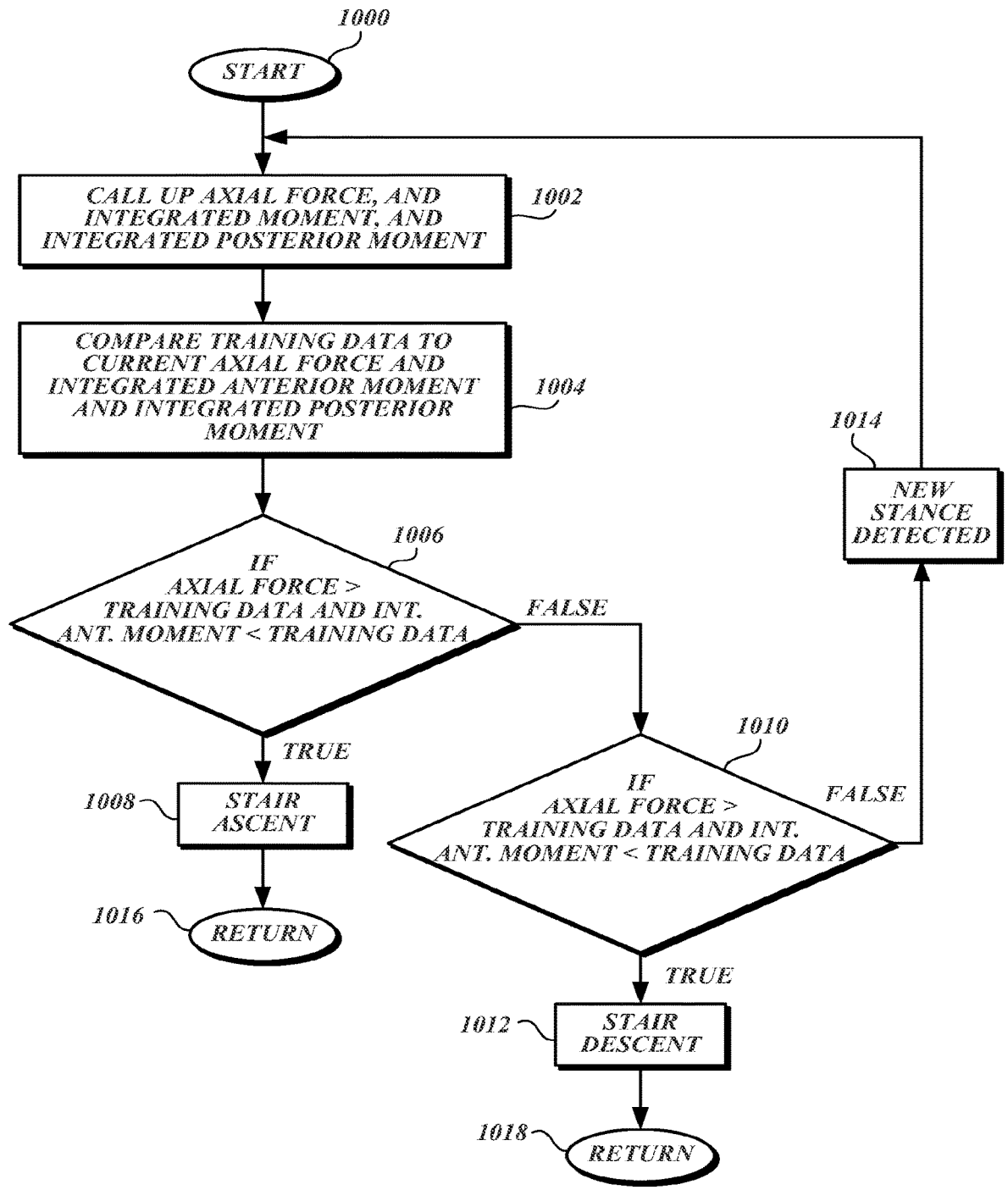
FIG. 15 is a flow diagram of the control scheme used in the prosthetic foot and ankle joint with hydraulic actuators of FIG. 1.

Referring to FIG. 15, a method is illustrated for determining when a patient is ascending stairs, block 331, and descending stairs, block 332. The method may be performed in the evaluation block 316 of FIG. 12. The method begins in start block 1000. From start block 1000, the method enters block 1002. In block 1002, the method has at this point recognized a stance phase has occurred and has qualified the stance phase to be a true stance phase. Next, the method calls up the axial force and a value representing an anterior moment or a posterior moment. For example, the method looks for attenuation of anterior and posterior moments. In one embodiment, the method can calculate an integrated anterior moment and an integrated posterior moment from training data collected when the patient walks with the system in a normal gait during the training session. Integral has the meaning as understood in the math field of calculus, which is generally graphically defined as an area bounded by a curve of a function within a predefined interval. In this case, the integrated posterior moment can be the area bounded by a curve when a posterior moment is registered, i.e., the plot of posterior moment from heel contact to the crossover point, and the integrated anterior moment can be the area bounded by a curve when an anterior moment is registered, i.e., from the crossover point to toe-off. In one implementation, the axial force is generally a measure of force acting vertically and generally corresponds to the patient's weight when the patient is in the middle of the stance phase, which can correspond to the patient center of gravity being over the transducer.

From block 1002, the method enters block 1004. In block 1004, the method compares the axial force, the integrated anterior moment, and the integrated posterior moment gathered during a training session with the axial force, the integrated anterior moment, and the integrated posterior moment occurring in real time. It should be realized that the axial force, the integrated anterior moment, and the integrated posterior moment from training data can be a representative value, such as the average, or the mean, taking into consideration more than one stance event.

From block 1004, the method enters block 1006. In block 1006, the method makes a determination if the axial force is greater than the axial force collected during the training session, and whether the integrated posterior moment in real time is less than the integrated posterior moment evaluated from the training data. If the conditions are true, a determination is made that the patient is ascending stairs, block 1008. However, if one of the conditions is false, the method enters a second determination, block 1010.

In block 1010, the method determines if the axial force occurring in real time is greater than the axial force evaluated from the training data, and whether the integrated anterior moment occurring in real time is less than the integrated anterior moment evaluated from the training data. If the method determines that the conditions are true, a determination is made that the patient is descending stairs, block 1012. However, if one of the conditions is false, the method awaits the detection of a new stance phase, block 1014, and repeats the evaluation process to determine whether the new stance is a stair ascending state or a stair descending state. If a determination is made that the patient is ascending stairs, block 1008, or the patient is descending stairs, block 1012, the method returns to FIG. 11, and the ankle angle is adjusted, block 326.

It should be realized that the method illustrated in FIG. 15 is one embodiment for determining a stair ascending state and a stair descending state, it is to be appreciated that other methods exist that may be substituted. For example, instead of comparing the integrated anterior moment and the integrated posterior moment with training data corresponding to a normal gait, the method can compare any variables to training data collected while the patient was actually ascending stairs and descending stairs. In such a case, the system can determine stair ascending and descending by recognizing the similarity of one or more variables to the training data collected during stair ascending and descending. Also, posterior moment is less than normal when ascending stairs, while anterior moment is less than normal when descending stairs.

Figure 16:
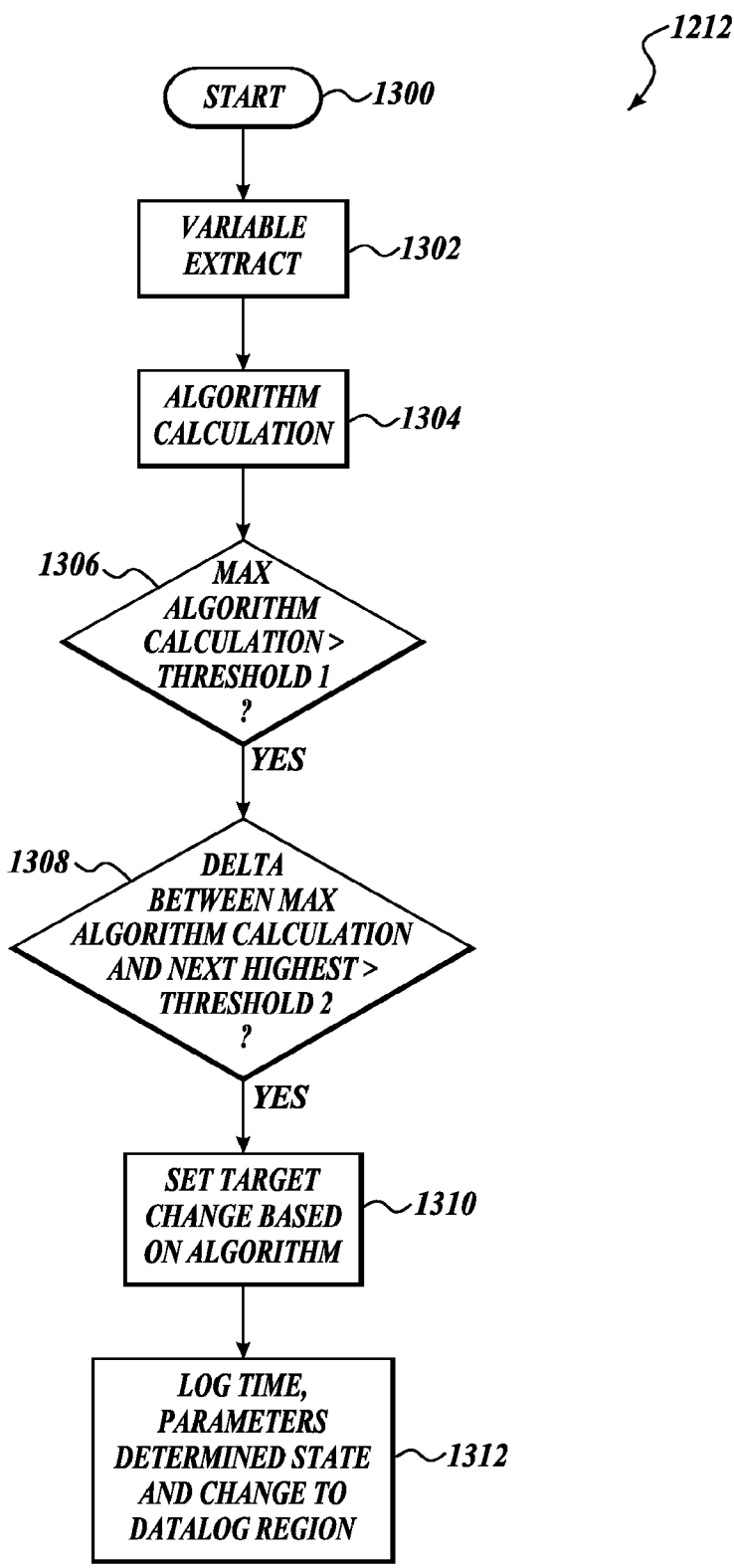
FIG. 16 is a flow diagram of the control scheme used in the prosthetic foot and ankle joint with hydraulic actuators of FIG. 1.

Referring to FIG. 16, a general method for improving on the accuracy of determining whether to make an adjustment to the ankle angle is illustrated. In this algorithm, a number is calculated, such as between 0 and 1, indicating the confidence of being in a state. A threshold value, such as greater than 0.5 can be used to determine that the patient is in the state. The threshold value can be changed so as to have a higher confidence that the patient is actually in the state the algorithm calculates; therefore, a threshold value of 0.6 or even greater may be used in some embodiments.

Block 1302 is for feature extraction. As described above, the use of variables, either sensed or calculated from other variables, are used as inputs in the sensing and processing system.

From block 1302, the method enters block 1304. In block 1304, an algorithm makes a calculation based on the features collected in block 1302 to determine a parameter or set of parameters occurring at any given state. From block 1304, the method enters block 1306. Block 1306 is a decision block for determining whether the maximum algorithm calculation is greater than a first threshold. If the determination is true, the method enters block 1308. Block 1308 is a decision block for determining whether the difference between the maximum algorithm calculation and the next highest calculation is greater than a second threshold. If the determination in block 1308 is true, the method enters block 1310. In block 1310, the microprocessor sets a target change of the plantarflexion angle based on the algorithm, which may include a set amount determined by a prosthetist. The microprocessor then commands the ankle joint 104 to open and/or close a valve to achieve the plantarflexion angle from the algorithm. From block 1310, the method enters block 1312. In block 1312, the microprocessor logs time, parameters, the determined state, and changes to a data log region of memory.

Based on the description herein, non-limiting examples of various embodiments are disclosed as follows.

A prosthetic foot assembly is disclosed. The assembly includes a pivoting ankle joint with a hydraulic system, a prosthetic foot connected to the distal side of the ankle joint, and at the proximal side, the ankle joint includes a transducer with an adaptor for attaching to a pylon. The pylon is connected to a socket that receives an amputated limb. The foot assembly includes a universal distal attachment allowing accommodation of various prosthetic feet.

The hydraulic system of the ankle joint includes a dual piston assembly with respective antagonistic cams, which remain in constant contact with pistons. The system includes a posterior piston and an anterior piston, respectively placed in front of and behind a pivoting connection. The pistons each include an integral accumulator with restrictors and check valves. An accumulator receives and releases hydraulic fluid gradually. For example, when hydraulic fluid enters a cylinder, the accumulator receives some hydraulic fluid, depending on the pressure and if the pressure overcomes the force of a spring restricting the entrance to the accumulator. In this case, the accumulator is a cylinder/subpiston within the main piston. Each piston has a sub-piston inside of which temperature compensation is provided by restricting flow to slow the flow rate rather than allowing angular movement to be "free" upon loading. This can be performed by: a) a small restrictor orifice or b) shear thickening fluid. Flow from the piston can be relieved through a one-way check valve to keep the pistons in constant contact with cams.

The heel (posterior) accumulator and toe (anterior) accumulator are restricted at different rates to accommodate differences in gait pattern (e.g., heel moment being significantly less than toe). Flow can be controlled through the use of a digital state valve with dual paths between the dual pistons/accumulators.

In one embodiment, the ankle joint can provide dorsiflexion bias for toe clearance. The compliance built in by compression of the accumulators allows the posterior piston to push up, and the anterior piston recedes to bring the toe up a small amount at swing phase. The spring force of the posterior accumulator can be greater than the spring force of the anterior accumulator.

Also disclosed are methods for controlling the ankle joint. The ankle joint/transducer provides data collection during the stance and swing phases of walking using, for example, strain gages and accelerometers.

The methods provide for real-time feature extraction. Key parameters are captured to which are applied linear, fuzzy logic, neural net, or generic algorithms to determine current state (walking flat, uphill, downhill etc.) in real time and execute changes to a plantarflexion angle between ankle and foot almost instantaneously (within first step, for example) based on those parameters. In some cases, a determination can be made prior to a complete step being recorded—certain conditions require or are highly dependant on only a single factor that is easily extracted sufficiently early in stance phase as to allow for initiation of accommodation while still in that stance phase.

Alternatively, parameters captured in the swing phase may provide sufficient indication as to allow preparatory valve positioning (opening) subject to confirmation of the stance phase data. In some methods, it is preferable that no decisions be made solely on swing phase accelerometry, but, in other embodiments, some changes may be "prepared" based on the swing phase and small changes executed with the possibility of correction if the swing phase data analysis was erroneous.

The methods may use natural moments induced in walking to affect microprocessor controlled changes. The methods use impedance control of joint position—instead of "forcing" the ankle to a given position, it is "allowed" to go to a given position under the natural moments induced by patient. A patient is anyone that wears the ankle joint. User is synonymous with patient.

The methods may use concurrent voting and confirmation using two or more algorithms.

In some embodiments, methods may use parameters only from the stance phase; in other embodiments, methods may use parameters only from the swing phase. In some embodiments, methods may use parameters from the stance phase and the swing phase.

In some embodiments, the prosthesis assembly may further include a passive knee joint with control of the passive knee based on the active ankle behavior. A fully passive or passive stance phase knee can be modified and may be controlled based on variations of ankle angle. This would be either standalone or bi-directional feedback to a controlled knee.

The ankle joint may include a digital bus connection to sensor system.

In some embodiments, the ankle joint can be constructed with multi-axial movement in the anterior/posterior plane and the right/left plane.

In some embodiments, the ankle joint may have the ability to document various key parameters that may be used to assess functionality levels, or to meet compliance with certain health organization's requirements. For example, the ankle joint may be configured to communicate with Internet-based products by recording data either through in-clinic testing or in-field recording of events and produce a report for the prosthetist for documentation of need—the ankle joint reduces moments at the socket by "X" percent when going up "Y" percent grade which correlates to "Z" effect on their long term health, where X, Y, and Z, are parameters determined by the specific organization or agency. Documentation could be a discrete in-office test of one slope, stairs, etc. or could be a field recording over the span of a month to indicate the effect the ankle joint has in a patient's normal life. "Patient" is used herein to mean any person wearing the ankle joint system.

In some embodiments, the ankle joint is in communication with a mobile phone or mobile device that the patient carries. A mobile phone or mobile device-based application can be used to view the current state, set preferred states (such as dependent on various shoes), override system logic, shutdown, and communicate with prosthetist via email or application.

In some embodiments, a method for controlling a prosthetic ankle joint employing a processor and a sensor, is disclosed. The method may include determining if a prosthetic ankle joint is weight bearing, if the prosthetic ankle joint is weight bearing, determining if a stance phase is qualified to be a true stance phase and of a patient ambulating, if the stance phase is qualified to be a true stance phase, determining a ground slope or a speed of the patient, controlling the angular alignment of the prosthetic ankle joint based on the ground slope or speed, and, if the prosthetic ankle joint is not weight bearing, locking or relaxing the ankle joint.

In some embodiments, the method may further include collecting training gait data from the patient with a normal gait, and comparing the training gait data to data that is collected when the ankle joint is weight bearing, and based on the comparison qualifying the stance phase.

In some embodiments, the method may further include collecting training gait data from the patient walking on a level ground and at a normal speed, and determining a home position for the ankle joint based on the level ground and normal speed.

In some embodiments, the method may further include controlling the ankle joint at the home position when a level ground slope is detected.

In some embodiments, the method may further include controlling the ankle joint at the home position when a normal speed is detected.

In some embodiments, the method may further include collecting training gait data from a patient with a normal gait, comparing the training gait data to data that is collected from the qualified stance phase, and, based on the comparison, detecting the ground slope or speed.

In some embodiments, the method may further include dorsiflexing the prosthetic ankle joint when the ground slope is detected to be uphill.

In some embodiments, the method may further include plantarflexing the prosthetic ankle joint when the ground slope is detected to be downhill.

In some embodiments, the method may further include dorsiflexing the prosthetic ankle joint when the patient is detected to be walking slowly.

In some embodiments, the method may further include plantarflexing the prosthetic ankle joint when the patient is detected to be walking fast.

In some embodiments, the method may further include determining if the patient is ascending stairs or descending stairs if the stance phase is qualified to be a true stance phase.

In some embodiments, the method may further include determining anterior moment and posterior moment during a stance phase, and comparing the anterior moment and posterior moment to training data.

In some embodiments, the method may further include detecting downhill when a maximum anterior moment is less than a maximum anterior moment of the training data, and a maximum posterior moment is greater than a maximum posterior moment of the training data.

In some embodiments, the method may further include detecting uphill when a maximum anterior moment is greater than a maximum anterior moment of the training data and a maximum posterior moment is less than a maximum posterior moment of the training data.

In some embodiments, the method may further include detecting ascending stairs when an axial force is greater than an axial force of the training data, and a posterior or anterior moment is greater than a posterior or anterior moment of the training data.

In some embodiments, the method may further include detecting descending stairs when an axial force is greater than an axial force of the training data and a posterior or anterior moment is greater than a posterior or anterior moment of the training data.

In some embodiments, the method may further include detecting if a keel angle is greater than a predetermined value and an anterior moment is greater than a predetermined value for a specified time period when the ankle joint is not weight bearing.

In some embodiments, the method may further include locking the ankle joint in response to detecting a keel angle is greater than a predetermined value and an anterior moment is greater than a predetermined value for a specified time period.

In some embodiments, the method may further include relaxing the ankle joint in response to not detecting a keel angle is greater than a predetermined value, and an anterior moment is greater than a predetermined value, for a specified time period.

In some embodiments, when the ankle joint is relaxed, the method may further include detecting at least one condition such as, the ankle joint is weight bearing, the ankle joint rate of motion exceeds a predetermined value, or the axial force rate of change exceeds a predetermined value, and in response to detecting the one condition, moving the ankle to a home position determined from training gait data.

In some embodiments, the method may further include plantarflexing the ankle joint when a posterior moment is sensed during a stance phase.

In some embodiments, the method may further include dorsiflexing the ankle joint when an anterior moment is sensed during a stance phase.

In some embodiments, the method may further include determining if a swing phase is qualified to be a true swing phase of a patient ambulating, and, if the stance phase and swing phase are qualified to be a true stance phase and swing phase of a person ambulating, determining a ground slope or a speed of the patient.

In some embodiments, the method may further include collecting training gait data from the patient with a normal gait, and comparing the training gait data to data that is collected when the ankle joint is weight bearing, and, based on the comparison, qualifying the stance and swing phase.

In some embodiments, the method may further include collecting training gait data from a patient with a normal gait, comparing the training gait data to data that is collected from the qualified stance and swing phase, and, based on the comparison, detecting the ground slope or speed.

In the embodiments of the method described, the various embodiments may include one, more than one, or all of the features of the other embodiments.

In some embodiments, a prosthetic ankle joint is disclosed. The ankle joint may include a base having a pivot secured to a body, a first and second piston in contact with the base, the body having a first and second cylinder within which the first and second pistons are placed, wherein the first cylinder and piston are placed anteriorly to the pivot, and the second cylinder and piston are placed posteriorly to the pivot, a hydraulic system connecting the first and second cylinders, wherein the system comprises one or more values to control transfer of fluid between the first and second cylinders, and a processor programmed with instructions to control the one or more valves.

In some embodiments, the prosthetic ankle joint may further include a first and second cam on the base, wherein the first cam supports the first piston, and the second cam supports the second piston, and the cams have a parabolic upper surface.

In some embodiments, the prosthetic ankle joint may further include in the first and second piston, a hydraulic fluid accumulator comprising a subpiston, and a spring biasing the subpiston within a chamber, wherein the chamber is allowed to receive and expel hydraulic fluid to and from the cylinder corresponding with the accumulator.

In some embodiments, the prosthetic ankle joint may further include a transducer connected to the upper side of the ankle joint, and a foot connected to the lower side of the base.

In the embodiments of the prosthetic ankle joint described, the various embodiments may include one, more than one, or all of the features of the other embodiments.

Following long-standing patent law, the words "a" and "an," when used in the claims or specification, denotes one or more, unless specifically noted.

While illustrative embodiments have been illustrated and described, it will be appreciated that various changes can be made therein without departing from the spirit and scope of the invention. For example, while the hydraulic system is used in an ankle joint, the system may be used in other applications and for other prosthetic joints.

The invention claimed is:

1. A prosthetic ankle joint, comprising:
a base;
a body connected to the base with a pivot, the body having a first cylinder and a second cylinder;
a first piston positioned in the first cylinder at a location anterior of the pivot and a second piston positioned in the second cylinder at a location posterior of the pivot;
a first cam and a second cam positioned on the base, the first cam supporting the first piston, and the second cam supporting the second piston;
a hydraulic system connecting the first and second cylinders, the hydraulic system including one or more valves to control transfer of fluid between the first and second cylinders, the one or more valves being manually adjustable.

2. The prosthetic ankle joint of claim 1, wherein the one or more valves is manually adjustable to separately adjust dorsi flexion and plantar flexion.

3. The prosthetic ankle joint of claim 1, further comprising a first hydraulic fluid accumulator in the first piston and a second hydraulic fluid accumulator in the second piston, wherein the first and second accumulators each comprise a subpiston and a spring biasing the subpiston within a chamber, wherein the chamber of the first accumulator receives and expels hydraulic fluid to and from the first cylinder, and the chamber of the second accumulator receives and expels hydraulic fluid to and from the second cylinder.

4. The prosthetic ankle joint of claim 1, further comprising a transducer connected to an upper side of the ankle joint and a foot connected to a lower side of the base.

5. The prosthetic ankle joint of claim 4, wherein the transducer includes one or more accelerometers, angle sensors, temperature sensors, and strain gauges.

6. The prosthetic ankle joint of claim 1, wherein the transducer includes an adaptor to couple the ankle joint to a pylon.

7. The prosthetic ankle joint of claim 6, wherein the transducer is operable to detect moments acting between the pylon and the ankle joint.

8. The prosthetic ankle joint of claim 1, wherein the first and second cams each have a parabolic upper surface.

9. The prosthetic ankle joint of claim 1, further comprising a processor, the processor being operable to control the one or more valves to dorsiflex the ankle joint when a ground slope a patient wearing the ankle joint is traversing is detected to be uphill.

10. The prosthetic ankle joint of claim 1, further comprising a processor, the processor being operable to control the one or more valves to plantarflex the ankle joint when a ground slope a patient wearing the ankle joint is traversing is detected to be downhill.

11. The prosthetic ankle joint of claim 1, further comprising a processor, the processor being operable to control the one or more valves to dorsiflex the ankle joint when a patient wearing the ankle joint is detected to be walking slow.

12. The prosthetic ankle joint of claim 1, further comprising a processor, the processor being operable to control the one or more valves to plantarflex when a patient wearing the ankle joint is detected to be walking fast.

13. The prosthetic ankle joint of claim 1, further comprising a processor, the processor being operable to control the one or more valves to plantarflex when a posterior moment is sensed during a stance phase during use of the ankle joint by a patient.

14. The prosthetic ankle joint of claim 1, further comprising a processor, the processor being operable to control the one or more valves to dorsiflex when an anterior moment is sensed during a stance phase during use of the ankle joint by a patient.

15. A prosthetic ankle joint, comprising:
a base;
a body connected to the base with a pivot, the body having a first cylinder and a second cylinder;
a first piston positioned in the first cylinder at a location anterior of the pivot and a second piston positioned in the second cylinder at a location posterior of the pivot;

a first cam and a second cam positioned on the base, the first cam supporting the first piston, and the second cam supporting the second piston;

a hydraulic system connecting the first and second cylinders, the hydraulic system including one or more valves to control transfer of fluid between the first and second cylinders based on at least one of:
 a timing or speed input;
 a moment or force input;
 an acceleration input;
 an ankle angle input.

16. The prosthetic ankle joint of claim 15, wherein the hydraulic system includes at least one manually controlled valve to control transfer of fluid between the first and second cylinders, and at least one electronically controlled valve to control transfer of fluid between the first and second cylinders.

17. The prosthetic ankle joint of claim 16, wherein the mechanical torque or force input has a threshold value for the at least one electronically controlled valve to open, the threshold value being manually adjustable.

18. The prosthetic ankle joint of claim 15, further comprising a transducer connected to an upper side of the ankle joint and a foot connected to a lower side of the base.

19. The prosthetic ankle joint of claim 18, wherein the transducer includes one or more of an accelerometer, angle sensor, temperature sensor, and strain gauge.

20. The prosthetic ankle joint of claim 18, wherein the transducer includes an adaptor to couple the ankle joint with a pylon, and is operable to detect moments acting between the pylon and the ankle joint.

* * * * *